US008396558B2

(12) United States Patent
Keller et al.

(10) Patent No.: US 8,396,558 B2
(45) Date of Patent: Mar. 12, 2013

(54) METHODS FOR TREATING CENTRAL PAIN SYNDROME AND OTHER PAIN RELATED PATHOLOGIES

(75) Inventors: Asaf Keller, Baltimore, MD (US); Radi Masri, Ellicott City, MD (US); Raimi Quiton, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 466 days.

(21) Appl. No.: 12/699,918

(22) Filed: Feb. 4, 2010

(65) Prior Publication Data
US 2010/0204751 A1    Aug. 12, 2010

Related U.S. Application Data

(60) Provisional application No. 61/151,608, filed on Feb. 11, 2009.

(51) Int. Cl.
*A61N 1/04* (2006.01)
*A61N 1/05* (2006.01)
*A61N 1/34* (2006.01)
*A61N 1/36* (2006.01)

(52) U.S. Cl. .......................................... 607/46
(58) Field of Classification Search ................ 607/46
See application file for complete search history.

(56) References Cited

U.S. PATENT DOCUMENTS

| | | | |
|---|---|---|---|
| 5,713,922 A | 2/1998 | King | |
| 6,484,059 B2 * | 11/2002 | Gielen | 607/45 |
| 6,493,576 B1 * | 12/2002 | Dankwart-Eder | 600/544 |
| 6,567,702 B1 * | 5/2003 | Nekhendzy et al. | 607/46 |
| 6,735,475 B1 * | 5/2004 | Whitehurst et al. | 607/46 |
| 6,782,292 B2 * | 8/2004 | Whitehurst | 607/45 |
| 7,010,351 B2 * | 3/2006 | Firlik et al. | 607/45 |
| 7,013,177 B1 * | 3/2006 | Whitehurst et al. | 607/46 |
| 7,302,298 B2 * | 11/2007 | Lowry et al. | 607/116 |
| 7,346,382 B2 | 3/2008 | McIntyre et al. | |
| 7,422,555 B2 * | 9/2008 | Zabara | 600/9 |
| 7,437,196 B2 * | 10/2008 | Wyler et al. | 607/48 |
| 7,623,927 B2 * | 11/2009 | Rezai | 607/45 |
| 7,657,316 B2 * | 2/2010 | Jaax et al. | 607/45 |
| 2005/0010262 A1 * | 1/2005 | Rezai et al. | 607/46 |
| 2005/0033379 A1 * | 2/2005 | Lozano et al. | 607/45 |
| 2005/0102006 A1 * | 5/2005 | Whitehurst et al. | 607/46 |
| 2006/0041242 A1 * | 2/2006 | Stypulkowski | 604/503 |
| 2006/0100671 A1 * | 5/2006 | Ridder | 607/45 |
| 2006/0190056 A1 * | 8/2006 | Fowler et al. | 607/45 |
| 2008/0215101 A1 * | 9/2008 | Rezai et al. | 607/3 |

(Continued)

OTHER PUBLICATIONS

Poster session abstract and lay summary for "Zona incerta: a certain role in central pain", by R.M. Masri et al., presented at Neuroscience 2008, held on Nov. 15-19, 2008 by the Society for Neuroscience, retrieved at http://0-www.sfn.org.ilsprod.lib.neu.edu/am2008/application/OmniPress/data/papers/Abstract_0170.htm.*

(Continued)

*Primary Examiner* — Carl H Layno
*Assistant Examiner* — Erin Piateski
(74) *Attorney, Agent, or Firm* — Roylance, Abrams, Berdo & Goodman, L.L.P.

(57) ABSTRACT

Central pain syndrome (CPS) is a debilitating condition that affects a large number of patients with a primary lesion or dysfunction in the central nervous system. Despite its discovery over a century ago, the pathophysiology underlying the development and maintenance of CPS is poorly understood. The present invention is drawn to novel methods of treating CPS. In certain aspects, the invention is drawn to the novel discovery of the role of the zona incerta (ZI) in CPS and methods of exploiting this novel discovery for the treatment of CPS.

14 Claims, 14 Drawing Sheets

A

B

U.S. PATENT DOCUMENTS

| | | | |
|---|---|---|---|
| 2008/0255632 A1* | 10/2008 | Rezai | 607/46 |
| 2009/0076567 A1* | 3/2009 | Fowler et al. | 607/45 |
| 2009/0112278 A1* | 4/2009 | Wingeier et al. | 607/45 |
| 2009/0163976 A1* | 6/2009 | Borckardt et al. | 607/46 |
| 2009/0292344 A1* | 11/2009 | Lowry et al. | 607/116 |

OTHER PUBLICATIONS

Attal, N. et al., Effects of IV morphine in central pain: a randomized placebo-controlled study, Neurology (2002) 58:554-563.

Baastrup, C. et al., Pharmacological management of neuropathic pain following spinal cord injury, CNS Drugs (2008) 22(6):455-475.

Barbaresi, P. et al., GABAergic neurons are present in the dorsal col. nuclei but not in the ventroposterior complex of rats, Brain Res. (1986) 382:305-326.

Bokor, H. et al., Selective GABAergic control of higher-order thalamic relays, Neuron (2005) 45:929-940.

Craig, A., Distribution of trigeminothalamic and spinothalamic lamina I terminations in the macaque monkey, J. Comp. Neurol. (2004) 477:119-148.

Dammerman, R. et al., An excitatory GABAergic plexus in developing neocortical layer 1, J. Neurophysiol. (2000) 84:428-434.

Defrin, R. et al., Pain following spinal cord injury, Spinal Cord (2002) 40:96-7; author reply 98-9.

Defrin, R. et al., Sensory determinants of thermal pain, Brain (2002) 125:501-510.

Diamond, M. et al., Somatic sensory responses in the rostral sector of the posterior group (POm) and in the ventral posterior medial nucleus (VPM) of the rat thalamus: dependence on the barrel field cortex, J. Comp. Neurol. (1992) 319:66-84.

Eide, P. et al., Central dysesthesia pain after traumatic spinal cord injury is dependent on N-methyl-D-aspartate receptor activation, Neurosurgery (1995) 37:1080-1087.

Endo, T. et al., Functional MRI of the brain detects neuropathic pain in experimental spinal cord injury, Pain (2008) 138:292-300.

Guido, W. et al., Receiver operating characteristic (ROC) analysis of neurons in the cat's lateral geniculate nucleus during tonic and burst response mode, Visual Neuroscience (1995) 12:723-741.

Lavallee, P. et al., Feedforward inhibitory control of sensory information in higher-order thalamic nuclei, J. Neurosci. (2005) 25(33):7489-7498.

Lee, J.I. et al., Pain and temperature encoding in the human thalamic somatic sensory nucleus (Ventral caudal): inhibition-related bursting evoked by somatic stimuli, J. Neurophysiol. (2005) 94:1676-1687.

Ling, C.Y. et al., Afferents from the colliculus, cortex, and retina have distinct terminal morphologies in the lateral posterior thalamic nucleus, J. Comp. Neurol. (1997) 388:467-483.

Liu, X.B. et al., Predominance of corticothalamic synaptic inputs to thalamic reticular nucleus neurons in the rat, J. Comp. Neurol. (1999) 414:67-79.

Lu, S.M. et al., Effects of membrane voltage on receptive field properties of lateral geniculate neurons in the cat: contributions of the low-threshold $Ca^{2+}$ conductance, J. Neurophysiol. (1992) 68:2185-298.

Masri, R. et al., Encoding of stimulus frequency and sensor motion in the posterior medial thalamic nucleus, J. Neurophysiol. (2008) 100:681-689.

Masri, R. et al., Cholinergic regulation of the posterior medial thalamic nucleus, J. Neurophysiol. (2006) 96:2265-2273.

Mills, C. et al., Changes in exploratory behavior as a measure of chronic central pain following spinal cord injury, J. Neurotrauma (2001) 18:1091-1105.

Mitrofanis, J., Some certainty for the "zone of uncertainty"? Exploring the function of the zona incerta, Neuroscience (2005) 130:1-15.

Nicolelis, M. et al., Somatotopic maps within the zona incerta relay parallel GABAergic somatosensory pathways to the neocortex, superior colliculus, and brainstem, Brain Res. (1992) 577:134-141.

Nicolelis, M. et al., Development of direct GABAergic projections from the zona incerta to the somatosensory cortex of the rat, Neuroscience (1995) 65:609-631.

Pierret, T. et al., Parallel streams for the relay of vibrissal information through thalamic barreloids, J. Neurosci. (2000) 20(19):7455-7462.

Porro, C. et al., Independent time courses of supraspinal nociceptive activity and spinally mediated behavior during tonic pain, Pain (2003) 104:291-301.

Power, B. et al., Ultrastructure of afferents from the zona incerta to the posterior and parafascicular thalamic nuclei of rats, J. Comp. Neurol. (2002) 451:33-44.

Sceniak, M. et al., Cellular actions of urethane on rat visual cortical neurons in vitro, J. Neurophysiol. (2006) 95:3865-3874.

Shaw, V. et al., Lamination of spinal cells projecting to the zona incerta of rats, J. Neurocytol. (2001) 30:695-704.

Sherman, S. Dual response modes in lateral geniculate neurons: mechanisms and functions, Vis. Neurosci. (1996) 13:205-213.

Siddall, P. et al., Allodynia following traumatic spinal cord injury in the rat, Neuroreport (1995) 6:1241-1244.

Stormer, S. et al., Chronic pain/dysaesthesiae in spinal cord injury patients: results of a multicentre study, Spinal Cord (1997) 35:446-455.

Trageser, J. et al., State-dependent gating of sensory inputs by zona incerta, J. Neurophysiol. (2006) 96:1456-1463.

Trageser, J. et al., Reducing the uncertainty: gating of peripheral inputs by zona incerta, J. Neurosci. (2004) 24:8911-8915.

Varela, C. et al., Differences in response to muscarinic activation between first and higher order thalamic relays, J. Neurophysiol. (2007) 98:3538-3547.

Veinante, P. et al., Thalamic projections from the whisker-sensitive regions of the spinal trigeminal complex in the rat, J. Comp. Neurol. (2000) 420:233-243.

Villarreal, C. et al., Antinociception induced by stimulating the anterior pretectal nucleus in two models of pain in rats, Clin. Exp. Pharmacol. Physiol. (2004) 31:608-613.

Villarreal, C. et al., Modulation of persistent nociceptive inputs in the anterior pretectal nucleus of the rat, Pain (2007) 132:42-52.

Wang, G. et al., Maladaptive homeostatic plasticity in a rodent model of central pain syndrome: thalamic hyperexcitability after spinothalamic tract lesions, J. Neurosci. (2008) 28(46):11959-11969.

Weng, H. et al., Physiological changes in primate somatosensory thalamus induced by deafferentation are dependent on the spinal funiculi that are sectioned and time following injury, Neuroscience (2003) 116:1149-1160.

Yen, C.T. et al., Distribution of thalamic nociceptive neurons activated from the tail of the rat, Brain Res. (1989) 498:118-122.

Ren, K., An improved method for assessing mechanical allodynia in the rat, Physiol. Behav. (1999) 67(5):711-716.

Dostrovsky, J. et al., Nociceptive responses in medial thalamus of the normal and arthritic rat, Pain (1990) 40:93-104.

* cited by examiner

METHODS FOR TREATING CENTRAL PAIN SYNDROME AND OTHER PAIN RELATED PATHOLOGIES

This application claims the benefit of U.S. Provisional Application Ser. No. 61/151,608, filed Feb. 11, 2009, which is hereby incorporated by reference in its entirety.

STATEMENT REGARDING FEDERALLY SPONSORED RESEARCH OR DEVELOPMENT

This invention was made with government support under NIH Grant No. NS-051799 awarded by National Institutes of Health. The government has certain rights in the invention.

BACKGROUND OF INVENTION

Central pain is defined as "pain initiated or caused by a primary lesion or dysfunction in the central nervous system" (Merskey and Bogduk, 1994). The diversity of clinical characteristics led to the designation of this condition as Central Pain Syndrome (CPS). The pain is most often steady and unrelenting, and has been described "as if knives heated in Hell's hottest corner were tearing me to pieces" (Head and Holmes, 1911). It has no cure and is often resistant to conventional pharmacological treatment (Baastrup and Finnerup, 2008). CPS can result from a variety of conditions, and these may produce lesions at any level along the spinal cord or the brain. Common conditions include, for example, spinal cord injuries, multiple sclerosis (MS) and cerebrovascular lesions (stroke). The prevalence of CPS in these conditions is alarmingly high. A majority of spinal cord injury patients, almost 30% of MS patients, and nearly 10% of stroke patients suffer from CPS (Bonica, 1991; Yezierski, 2000; Boivie, 2005).

Many of the earliest reported cases of CPS involved damage to the thalamus (Edinger, 1891; Dejerine and Roussy, 1906; Head and Holmes, 1911). As a result, thalamic lesions were thought to be required for development of pain, and the syndrome was referred to for decades by the misleading term "thalamic pain". Research since that time has established that CPS can result from damage to any structure along spinothalamo-cortical pathways that convey pain and temperature information (Schmahmann and Leifer, 1992; Bowsher, 1996; McGowan et al., 1997; Peyron et al., 2000; Finnerup et al., 2003; Boivie, 2005; Kim et al., 2007).

Immediately following spinal cord injury or stroke, somatosensation, including pain, is reduced (hypoalgesia). In most patients, pain starts within a few weeks after the original insult, and includes both increased pain with noxious stimulation (hyperalgesia) and pain in response to previously innocuous stimuli (allodynia). Perhaps most debilitating— and puzzling—is the presence, in the majority of patients, of spontaneous pain (Tasker, 1991; Greenspan et al., 2004; Boivie, 2005; Baliki et al., 2007).

One hypothesis that remains in favour of CPS, almost a century since it was first formulated, is that CPS results from abnormally suppressed inhibition in the thalamus (Head and Holmes, 1911). Unfortunately, any consensus appears to end there, as there are conflicting findings and hypotheses regarding the mechanisms and site of operation of this disinhibition (see Boivie, 2005; Canavero and Bonicalzi, 2007). To this end, there is a need in the art for determining mechanisms and targets for treatment of CPS. The inventors of the present invention have now discovered a novel mechanism and target for CPS. The inventors demonstrate herein that CPS results from, and can be treated by correcting, suppressed firing of inhibitory inputs from the inhibitory nucleus zona incerta (ZI) to the posterior thalamus (PO).

BRIEF SUMMARY OF INVENTION

The invention relates to neurophysiology. The invention further relates to pathophysiology related to pain. The invention even further relates to a method of treating pain (including, for example, CPS, hyperalgesia, and allodynia).

In certain aspects, the invention is drawn to a method of treating a symptom of central pain syndrome (CPS) in an individual in need thereof comprising stimulating a region of the brain wherein said region comprises the zona incertia (ZI). In further aspects, the region comprising the ZI consists of the ZI.

In certain aspects, the invention is drawn to a method of treating hyperalgesia in an individual in need thereof comprising stimulating a region of the brain wherein said region comprises the zona incertia (ZI). In further aspects, the region comprising the ZI consists of the ZI.

In certain aspects, stimulating a region of the brain is accomplished by electrical stimulation. In further aspects, electrical stimulation is performed either transcranially or subcranially. In even further aspects, electrical stimulation is performed subcranially. In even other further aspects, electrical stimulation that is performed subcranially is achieved by an electrode implanted directly in the ZI.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific aspect disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only, and is by no means intended to define the limits of the invention.

DETAILED DESCRIPTION OF THE INVENTION

I. Definitions

Figure 1A:
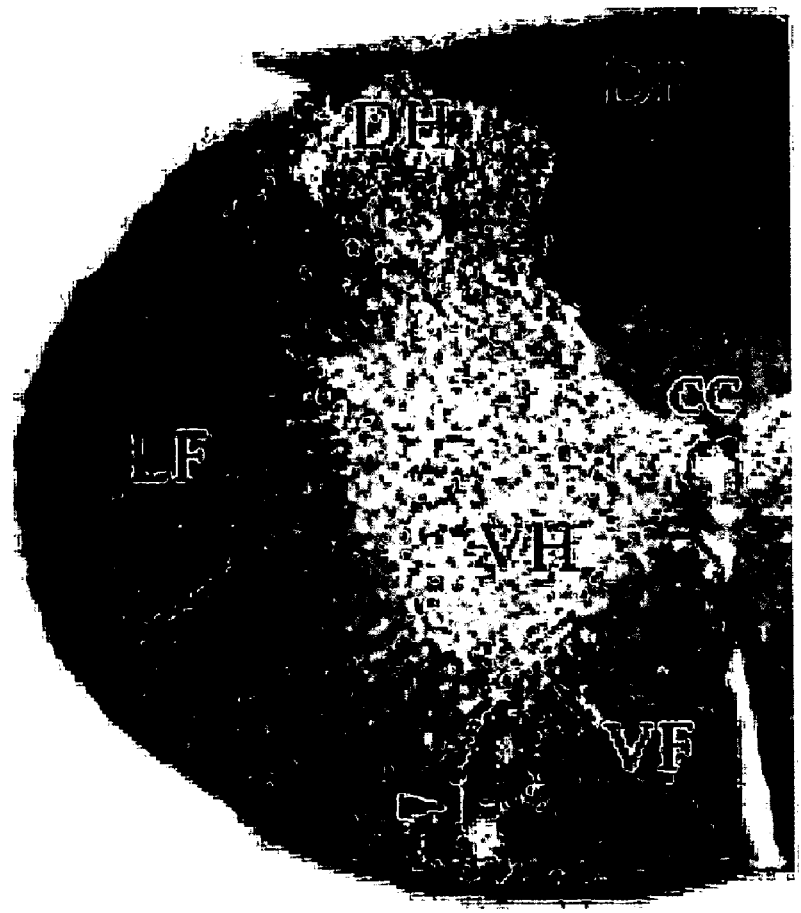
FIG. 1. Spinal cord lesions. (A) Coronal section through the cervical spinal cord showing a representative lesion site (arrowhead) involving the STT. (B) A line drawing summarizing the location and size of spinal lesions in animals with mechanical hyperalgesia (unfilled areas). Shaded areas represent the location of ascending STT axons, adapted from FIG. 5 in Geisler et al., (1991). CC: Central canal, DH: Dorsal horn, DF: Dorsal funiculus, LF: Lateral funiculus, VH: Ventral horn, VF: Ventral funiculus. Scale bar: 300 µm.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, "treat" and all its forms and tenses (including, for example, treat, treating, treated, and treatment) refer to therapeutic treatment, prophylactic or preventative treatment, and management of a pathological condition of the invention (including, for example, CPS, hyperalgesia, and allodynia). An individual in need thereof of treatment include those already with a pathological condition of the invention (including, for example, CPS, hyperalgesia, and allodynia) as well as those in which a pathological condition of the invention is to be prevented or managed.

II. The Present Invention

The rat model used in our study (Wang and Thompson, 2008a) recapitulates several diagnostic signs of CPS. Immediately following spinal lesions that involve the spinothalamic tract (STT), the rats display transient mechanical hypoalgesia below and unilateral to the lesion, and, within two to three weeks, they developed bilateral hyperalgesia below the lesion. In addition, cold hyperalgesia appeared within 14 days in the hindpaw ipsilateral to the lesion. The time course of these changes, the presence of bilateral mechanical hyperalgesia, and the reversal of hyperalgesia by a centrally acting opiate, are all consistent with pathophysiology in supraspinal structures. All rats that developed CPS had lesions within the STT, consistent with the obligatory role of insults to the spinothalamocortical pathway in the pathophysiology of CPS (Canavero and Bonicalzi, 2007).

Support for a role of supraspinal pathophysiology comes from the finding that activity in two major targets of the STT, the spinal trigeminal nucleus, a main source of afferent inputs to the PO, and the VPL, were unaffected by spinal lesions. The inventors cannot exclude the possibility that the lesions affected other spinal nuclei or ascending and descending tracts, or the possibility that damage to these regions might contribute to the clinical signs of CPS. Nevertheless, regardless of the precipitating insult, this model provides clear evidence of the role that the ZI and the PO occupy in the pathophysiology of CPS.

The ZI sends a dense GABAergic projection to the posterior nucleus of the thalamus (PO) (Power et al., 1999; Bartho et al., 2002), a nucleus critically involved in nociceptive processing (Poggio and Mountcastle, 1960; Casey, 1966; Apkarian and Shi, 1994; Zhang and Giesler, 2005). In certain aspects of the invention, the ZI is stimulated directly by electrical stimulation, which causes, for example, an increase in GABAergic neuron firing (including, for example, GABAergic neurons projecting to the PO). In other aspects of the invention, the ZI is stimulated indirectly by stimulating another brain region or nucleus which causes, for example, an increase in ZI GABAergic neuron firing (including, for example, GABAergic neurons projecting to the PO). Indirect stimulation can be achieved, for example, by electrically stimulating the motor cortex, which causes stimulation of the ZI. Indirect stimulation can be achieved either electrically or by the administration of a molecule with biological activity. Electrical stimulation encompassed by the instant invention is any amount of electrical stimulation that can increase the firing rate of ZI neurons (including, for example, GABAergic neurons projecting to the PO) or decrease the firing rate of PO neurons. This can be achieved by, for example, direct electrical stimulation (or indirect stimulation resulting in the equivalent) of the ZI at a frequency range of 0.1 Hz to 1000 Hz, intensity range of 1 µA to 1 mA, or any combination therein. Both long trains of stimuli, or patterned stimuli (including, for example, theta burst stimulation) can be used.

In certain aspects of the invention, the frequency range is between about 0.1 Hz to 900 Hz, 0.1 Hz to 800 Hz, 0.1 Hz to 700 Hz, 0.1 Hz to 600 Hz, 0.1 Hz to 500 Hz, 0.1 Hz to 400 Hz, 0.1 Hz to 300 Hz, 0.1 Hz to 200 Hz, 0.1 Hz to 100 Hz, 1 Hz to 900 Hz, 1 Hz to 800 Hz, 1 Hz to 700 Hz, 1 Hz to 600 Hz, 1 Hz to 500 Hz, 1 Hz to 400 Hz, 1 Hz to 300 Hz, 1 Hz to 200 Hz, 1 Hz to 100 Hz, 10 Hz to 100 Hz, 20 Hz to 100 Hz, 30 Hz to 100 Hz, 40 Hz to 100 Hz, 50 Hz to 100 Hz, 60 Hz to 100 Hz, 70 Hz to 100 Hz, 80 Hz to 100 Hz, and 90 Hz to 100 Hz. In further certain aspects of the invention, the frequency range is between about 25 Hz to 75 Hz, 30 Hz to 70 Hz, 35 Hz to 65 Hz, 40 Hz to 60 Hz, and 45 Hz to 55 Hz.

In other certain aspects of the invention, the intensity range is between about 1 µA to 0.9 mA, 1 µA to 0.8 mA, 1 µA to 0.7 mA, 1 µA to 0.6 mA, 1 µA to 0.5 mA, 1 µA to 0.4 mA, 1 µA to 0.3 mA, 1 µA to 0.2 mA, 1 µA to 0.1 mA, 1 µA to 0.09 mA, 1 µA to 0.08 mA, 1 µA to 0.07 mA, 1 µA to 0.06 mA, 1 µA to 0.05 mA, 1 µA to 00.4 mA, 1 µA to 0.03 mA, 1 µA to 0.02 mA, and 1 µA to 0.01 mA. In further certain aspects of the invention, the intensity range is between about 1 µA to 10 µA, 2 µA to 9 µA, 3 µA to 8 µA, 4 µA to 7 µA, and 5 µA to 6 µA.

It is noted that certain aspects of stimulation (e.g., the mode, frequency, intensity, etc.) of the ZI has been provided herein for illustration purposes and in no way limits the invention since at least one novel and non-obvious aspect of the invention is the elucidation of a causative effect of ZI abnormalities and responses to pain, and the ability to modulate pain responses by stimulating the ZI.

Electrical stimulation of the ZI (either directly or indirectly) can be carried out, for example, with a subcranially implanted stimulating electrode or by a transcranial device or method (including, for example, transcranial magnetic stimulation). In certain aspects of the invention, a stimulating electrode may be placed within or directly adjacent to the ZI to provide for the electrical stimulus of the ZI that causes an increase in GABAergic neuron firing (including, for example, GABAergic neurons projecting to the PO). In other aspects of the invention, a transcranial device or method can be used to achieve electrical or magnetic stimulation of the ZI (for both subcranially implanted stimulating electrodes and transcranial devices and methods see, for example, U.S. Pat. No. 7,437,196; U.S. Pat. No. 7,422,555; U.S. Pat. No. 7,346,382; U.S. Pat. No. 7,302,298; U.S. Pat. No. 6,493,576; U.S. Pat. No. 6,484,059; U.S. Pat. No. 5,713,922; US Patent Application Publication No. 20090030480; US Patent Application Publication No. 20090024187; US Patent Application Publication No. 20090024044; US Patent Application Publication No. 20080312716; US Patent Application Publication No. 20080294033; US Patent Application Publication No. 20080269836; US Patent Application Publication No. 20080214920; US Patent Application Publication No. 20080208287; US Patent Application Publication No. 20080208283; US Patent Application Publication No. 20080154341; all of which are incorporated by reference in their entirety).

In certain aspects, the invention is drawn to the treatment of CPS, which has no cure or effective treatment. In other aspects, the invention is drawn to the treatment of hyperalgesia or allodynia that is associated with CPS and is not associated with CPS. Methods for treating hyperalgesia or allodynia are the same as those described for CPS (e.g., direct or indirect electrical stimulation of the ZI that causes an increase in GABAergic neuron firing (including, for example, GABAergic neurons projecting to the PO)). CPS is a neurological condition caused by damage to or dysfunction of the central nervous system (CNS), which includes the brain, brainstem, and/or spinal cord. CPS can be caused by, for example, a stroke, multiple sclerosis, a tumor, epilepsy, brain or spinal cord trauma (including, for example, traumatic brain injury), or Parkinson's disease. The character of the pain associated with this syndrome differs widely among individuals partly because of the variety of potential causes. CPS may affect a large portion of the body or may be more restricted to specific areas, such as hands or feet. Pain is typically constant, may be moderate to severe in intensity, and is often made worse by touch, movement, emotions, and temperature changes, usually cold temperatures. Individuals experience one or more types of pain sensations, the most prominent being burning. Mingled with the burning may be sensations of "pins and needles;" pressing, lacerating, or aching pain; and brief, intolerable bursts of sharp pain similar to the pain caused by a dental probe on an exposed nerve. Individuals may have numbness in the areas affected by the pain. The burning and loss of touch sensations are usually most severe on the distant parts of the body, such as the feet or hands. CPS often begins shortly after the causative injury or damage, but may be delayed by months or even years, especially if for example, it is related to post-stroke pain.

In aspects of the invention drawn to spinal cord injury, the spinal cord injury results in injury to the STT, which can be transient or permanent. In particular aspects, injury to the STT is anywhere along the spinal column. In other particular aspects, injury to the STT is between vertebrae C6 and T9.

The inventors discovered that the ZI plays an essential role in the pathophysiology of CPS. Consistent with this, the inventors found a significant suppression of both spontaneous and evoked activity in inhibitory neurons in the ZI and abnormally high spontaneous and evoked activity of neurons in the PO of animals with CPS. Furthermore, reduced hyperalgesia after electrical stimulation of the ZI and the positive association between behavioral and neurophysiological thresholds in rats with CPS is consistent with a causal role for suppressed incerto-thalamic inputs in CPS.

A role for the incerto-thalamic pathway in CPS is also consistent with previous findings demonstrating that, in normal rats, the ZI regulates both spontaneous and evoked activity of PO neurons (Trageser and Keller, 2004; Trageser et al., 2006) (see also Lavallee et al., 2005). The inventors considered the possibility that there is a reduction in other inhibitory inputs to the PO. There are no GABAergic interneurons within the PO (Barbaresi et al., 1986) and, therefore, all GABAergic inhibition is mediated by extrinsic afferents. An important source of these afferents is the GABAergic reticular nucleus of the thalamus (TRN), which has been hypothesized to play a role in CPS (Foix et al., 1922; Boivie, 2005). TRN does not receive does not receive ascending sensory inputs, and its major source of excitatory input is from somatosensory cortex (Liu and Jones, 1999). Pharmacological suppression or lesions of the somatosensory cortex—which eliminate sensory responses in TRN—fail to reveal short-latency responses in the PO (Diamond et al., 1992a). Therefore, GABAergic inhibition from TRN is unlikely to be involved in directly regulating PO responses. Further, GABAergic terminals in the PO that originate from the ZI differ from those of TRN origin by their larger size, the presence of multiple release sites, and multiple filamentous contacts, all features suggesting that the ZI exerts significantly more potent inhibition upon the PO (Bartho et al., 2002; Bokor et al., 2005). Moreover, the inventors demonstrated that responses evoked with innocuous stimuli in VPM and VPL—nuclei that receive inhibition exclusively from TRN—were unaffected by spinal lesions, which argues against a role for TRN in CPS.

The anterior pretectal nucleus (APT) also sends dense GABAergic inputs exclusively to higher-order thalamic nuclei, and it too can regulate the activity of PO neurons (Bokor et al., 2005). Further, both the ZI and APT receive dense nociceptive inputs through the STT (Apkarian and Hodge, 1989; Shaw and Mitrofanis, 2001; Craig, 2004), and both the ZI and APT have been implicated in a variety of pain-related functions (Yen et al., 1989; Porro et al., 2003; Villarreal et al., 2004; Villarreal and Prado, 2007). These findings suggest that APT might also be involved in the pathogenesis of CPS. Therefore, the inventors consider the ZI and/or APT to be the most parsimonious candidates providing inhibitory regulation of the PO. It is contemplated herein that APT, like that of ZI, activity is suppressed in CPS and that the instant invention also encompasses stimulating APT GABAergic projecting to the PO.

In addition to the PO, the ZI and APT innervate higher order thalamic nuclei that have been traditionally implicated in nociceptive processing, including the medial dorsal nucleus, the central median nucleus, nucleus submedius and the parafasicular nucleus (Craig and Burton, 1981; Bushnell and Duncan, 1989; Dostrovsky and Guilbaud, 1990; Power and Mitrofanis, 2002). It is possible that neuronal activity in these nuclei is enhanced in animals with CPS. Together with the PO, these nuclei project to cortical areas associated with the experience of pain (reviewed in Jones, 2007), and abnormalities in their neuronal activity—caused by reduced inhibition from the ZI and/or APT—may play an integral part in the development or maintenance of CPS. The invention described herein contemplates that the ZI and/or APT play an integral role in CPS and that stimulating either or both of these nuclei provides a novel method of treating CPS and other pain related pathophysiologies. Recordings of field potentials in brain slices taken from animals with CPS after spinal lesions reveal that bursting discharges are evoked in VPL in response to local electrical stimulation (Wang and Thompson, 2008a). The absence of abnormal VPL responses in the present experiments might be explained by differences in the nature of the stimulus or by the urethane anesthetic.

The ZI also projects to the somatosensory cortex (Nicolelis et al., 1995). ZI projections upon the neocortex are sparse in adult animals, and they preferentially target cortical layer I (Dammerman et al., 2000). Thus, cortical influences upon the PO are unlikely to be affected by suppression of ZI input to the cortex. Superior colliculus, and other structures inhibited by the ZI and/or APT, provide relatively sparse inputs to the PO, and are not thought to significantly shape its response properties (Ling et al., 1997).

It is possible that enhanced PO responses in CPS may be due to enhanced excitatory inputs, rather than or in addition to, reduced inhibition. The main sources of excitation to the PO are the spinal trigeminal nuclei, the spinal dorsal horn, and the somatosensory cortex (Diamond et al., 1992a; Pierret et al., 2000; Zhang and Giesler, 2005). The inventors found that neuronal responses in SpVi and SpVc were not affected by spinal lesions and thus are unlikely to contribute to changes in the PO. The inventors did not directly test the contribution of peripheral inputs from the dorsal horn or cortical inputs to the PO, and thus their involvement in CPS remains unknown. Similarly, the contribution of "modulatory" inputs, such as cholinergic or serotonergic afferents, cannot be excluded (Varela and Sherman, 2007). However, these spinal, cortical, and modulatory inputs also project upon the VPM and VPL nuclei, and evoked responses in these nuclei remain unchanged in animals with CPS. Therefore, the inventors conclude that disinhibition from the ZI and/or APT upon the PO and related nuclei is an important mechanism and target in the pathophysiology and treatment of CPS.

While the invention has been described with reference to certain particular aspects thereof, those skilled in the art will appreciate that various modifications may be made without departing from the spirit and scope of the invention. The scope of the appended claims is not to be limited to the specific aspects described herein.

Methods and Materials

Certain aspects of the invention have been carried out based on practices in the field of physiology and neurophysiology. Some of these methods are described herein. Others are known to those of ordinary skill in the art and have not been described herein, but are still considered for the purposes of, for example, enabling the invention.

Spinal Lesions

All procedures were conducted in accordance with Animal Welfare Act regulations and PHS guidelines. Strict aseptic surgical procedures were used, in accordance with the guidelines of the International Association for the Study of Pain, and were approved by the University of Maryland School of Medicine Animal Care and Use Committee. Thirty-four adult female Sprague-Dawley rats weighing 250-300 g were used. Animals were anesthetized with ketamine/xylazine (100/8 mg/kg; i.p), and the animals were placed on a thermo-regulated heating pad. A laminectomy to expose the spinal cord was performed and a quartz-insulated platinum electrode (5 μm tip) was targeted to the STT, based on stereotaxic coordinates, on one side of the spinal cord. DC current (10 μA for 10 sec, repeated 4 times) was passed through the electrode to produce an electrolytic lesion (approximately 0.6 mm3). Sham surgery was performed without performing laminectomy. The analgesic buprenorphine (0.05 mg/kg) was administered every 12 hours for 24 hours post-operatively (2 doses total).

Behavioral Testing

Cold withdrawal thresholds. Animals were tested for cold hyperalgesia at least 14 days after sham or lesion surgery. The animals were allowed to stand upright with the forepaws on the experimenter's hand. A thermo-regulated cold copper probe (2° C., 6 mm diameter) was applied to the hind paw ipsilateral to the lesion site. An experimenter, blind to the treatment, applied the probe to the dorsal surface of the paw and measured the latency to withdrawal. In control experiments, the same probe was applied without cooling to test that the animals withdrew their paws due to the cold temperature rather than the tactile sensation of the probe. Mann Whitney U test (MWU) was used to compare pre- and post-lesion data. Mechanical withdrawal thresholds. Animals were tested on three consecutive days before the lesion surgery, at day 3 post-surgery, at day 7 post-surgery, and at weekly intervals thereafter. To minimize the animals' anxiety they were habituated for two weeks prior to behavioral testing, and were trained to stand upright with the forepaws on the experimenter's hand. Calibrated von Frey filaments (Stoelting, Ill.) were applied to the hindpaw or the vibrissae pad. The inventors applied the filaments to the dorsal surface of the paws based on studies demonstrating that the dorsal approach more reliably and consistently detects threshold changes (Ren, 1999). Vibrissae pad stimuli were applied as described in (Ren, 1999). Mechanical withdrawal threshold was defined as the force at which the animal withdrew to 3 of the 5 stimuli delivered. Friedman test, followed by MWU test were used to compare pre- and post-lesion data. To determine the sample size, a power analysis was performed for all experiments using $\alpha=0.05$ and power=0.85.

Reversal of mechanical hyperalgesia. Buprenorphine hydrochloride (Hospira Inc., IL) was administered (i.p.) at three different concentrations (10, 30 and 75 µg/kg) to rats with behaviorally confirmed mechanical hyperalgesia at least 14 days after spinal surgery. Twenty minutes after administration, mechanical withdrawal thresholds to von Frey filaments were assessed at the hindpaws and the vibrissae pad, and compared to thresholds obtained before the administration of the drug. Behavioral testing was also repeated 24 hr later to confirm that the effects of buprenorphine were reversible.

ZI Stimulation

In a separate set of animals (n=6) after spinal surgery, chronic bipolar quartz-insulated tungsten electrodes were implanted in the ZI, contralateral to the spinal lesions. Approximately 3 weeks after the spinal and implantation surgeries, the animals developed mechanical hyperalgesia and exhibited signs of CPS as determined by the behavioral tests described above. The inventors then compared withdrawal thresholds to mechanical stimuli during periods of ZI stimulation (25 uA, 50 Hz, 300 µs square pulses for 20 min), with periods without ZI stimulation. In control experiments the animals were attached to the stimulator but no current was delivered. Only one experiment was performed per day and in each animal, the experiment was repeated 5 times for each condition (stimulation on or off). The experimenter was blinded to the conditions of the stimulation.

In Vivo Experiments

Extracellular recording. At least 14 days after surgery, rats were anesthetized with urethane (1.5 g/kg, i.p.) and prepared for extracellular recordings, as previously described (Masri et al., 2006; Masri et al., 2008). The inventors selected urethane as an anesthetic because it is the only anesthetic that has no, or negligible, effects on glutamatergic and GABAergic transmission, and therefore produces only minimal disruption, if any, of signal transmission in the neocortex (Sceniak and Maciver, 2006). The inventors digitized waveforms (40 kHz) recorded from well-isolated units through a PLEXON (Dallas, Tex.) data acquisition system, and sorted units off-line with PLEXON'S OFFLINE SORTER, using dual thresholds and principal component analyses. The inventors generated auto-correlograms with NEUROEXPLORER software (Littleton, Mass.) to confirm that the inventors obtained recordings from single units. Mechanical stimulation. The inventors recorded spontaneous activity and responses to a series of mechanical stimuli with forces that spanned the innocuous and noxious range (6 to 200 g) using an electronic von Frey anesthesiometer (IITC Inc., CA). Forces were applied to the dorsal hindpaw or the face, ipsilateral to the lesion site 10 times each in a randomized order. The inventors computed mean firing rate during spontaneous activity periods and during application of each level of mechanical stimulation. The inventors used repeated measures ANOVA followed by Dunnett's post hoc test to determine the lowest mechanical force that produced neuronal firing that differed significantly (p<0.05) from spontaneous activity.

Vibrissae stimulation. The inventors stimulated vibrissae ipsilateral to the lesion site with air puffs delivered through a tube, as in our previous studies (Magi et al., 2008). The inventors exported time stamps of well-isolated units and of stimulus triggers to MATLAB (MathWorks, Natick, Mass.) for analyses using custom-written algorithms. The inventors constructed peristimulus time histograms (PSTHs, 1 ms bins), and defined significant stimulus-evoked responses as PSTH bins whose response magnitude significantly exceeded (99% confidence interval) spontaneous activity levels, computed from a 200 ms period preceding the stimuli. The inventors performed statistical analyses in STATA (StataCorp LP., TX), and assessed, in individual neurons, changes occurring in sensory-evoked activity using the MWU test; p<0.05 was considered significant.

Burst analysis. The inventors identified bursts of action potentials as clusters of at least three spikes with interspike intervals of $\leq 4$ ms, in which the first spike in the burst has a preceding interspike interval of at least 100 ms (Lu et al., 1992; Guido et al., 1995; Sherman, 1996).

Identification of recording, stimulation and spinal lesion sites. The inventors marked recording sites by placing electrolytic lesions (5 µA for 10 sec) at the end of each experiment, then deeply anesthetized the rats and perfused them transcardially with buffered saline followed by 4% buffered paraformaldehyde. The inventors obtained coronal brain and spinal sections (70 µm thick) and Nissl-stained the sections to identify recording and lesion sites.

EXAMPLES

Example 1

Animal Model of Central Pain Syndrome

Figure 1B:
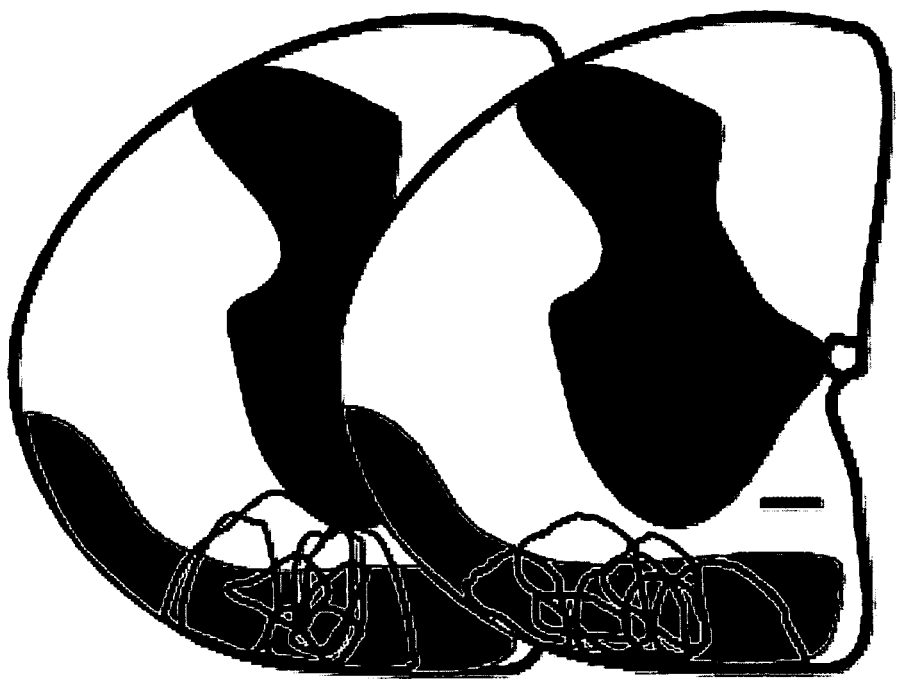

The inventors and others have previously shown that CPS develops in rats following lesions of the spinal cord (Siddall et al., 1995; Mills et al., 2001; Endo et al., 2008; Wang and Thompson, 2008b). Because the spinothalamocortical system is affected in all central pain patients, the inventors experimentally produced lesions that included the spinothalamic tract (STT). Rats (n=18) received a single, unilateral electrolytic lesion in the anterolateral quadrant of the spinal cord, at lower cervical to upper thoracic levels (FIG. 1A). In rats, STT afferents to medial and lateral thalamic nuclei travel in the ventral and ventrolateral funiculi of the spinal cord (Giesler et al., 1981). The inventors therefore targeted lesions to these spinal cord regions (FIG. 1B).

Figure 2A:
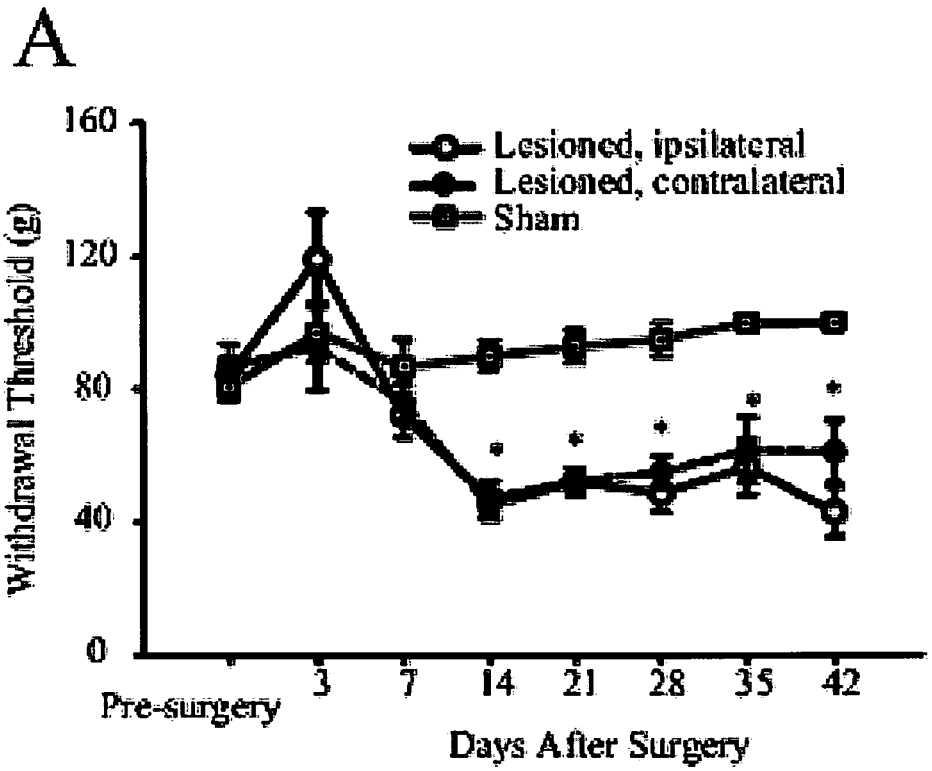
FIG. 2. Behavioral assessment of spinal-lesioned and sham-operated animals. (A) Hindpaw (dorsal surface) mechanical withdrawal thresholds decrease over time and hyperalgesia develops bilaterally after spinal lesions. (B) Stimulus-response curves collected before and 14 days after surgery. (C) Animals with spinal lesions responded at significantly shorter latencies to cold stimuli applied to the dorsal surface of ipsilateral hindpaw. (D) Systemic administration of the opiodergic drug buprenorphine hydrochloride, 14 days after spinal lesions, resulted in a dose-dependent reversal of hindpaw hyperalgesia in spinal-lesioned animals. (E) Mechanical hyperalgesia also develops bilaterally on the vibrissae pad. (F) Vibrissae pad mechanical hyperalgesia is reversed in a dose-dependent manner by systemic administration of the opiodergic drug buprenorphine hydrochloride, 14 days after spinal lesions. All values means±SEM. * statistically significant difference, p<0.05.
Figure 2B:
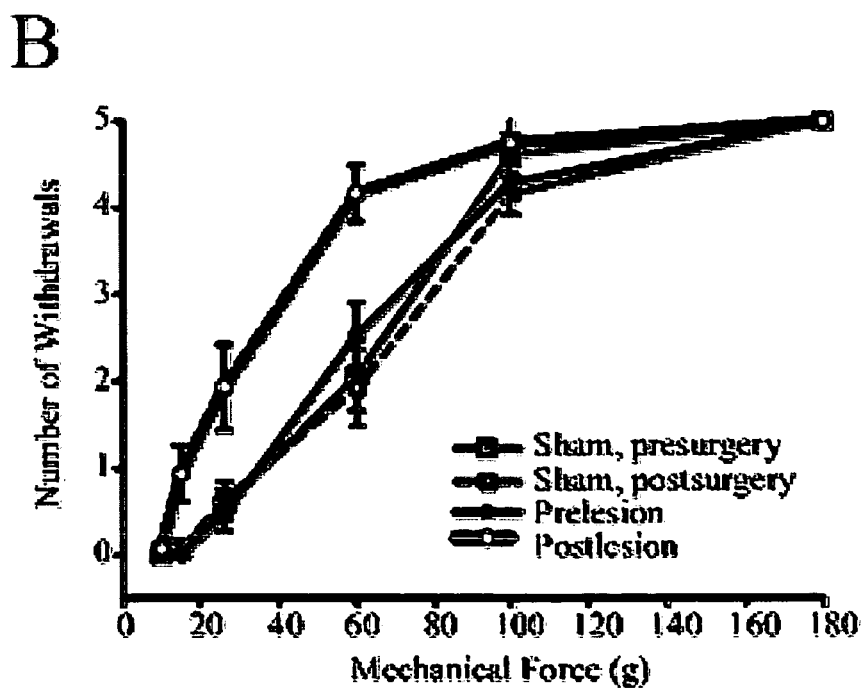

In spinal-lesioned animals—and in contrast to animals receiving sham surgery—hindpaw withdrawal thresholds to mechanical stimulation of the dorsal paw surface transiently increased (hypoalgesia) immediately after the lesion. Subsequently, significant reductions in thresholds (hyperalgesia) were evident bilaterally by 14 days post-lesion (FIG. 2A). Mechanical thresholds decreased from 84±22 g to 47±21 g (p=0.007, Friedman) on the ipsilateral hindpaw and from 86±29 g to 44±17 g (p=0.007) on the contralateral hindpaw. The reduction in withdrawal threshold was evident in 94% of spinal-lesioned animals and persisted for the duration of the experiments (up to 42 days; FIG. 2A). Stimulus-response curves constructed from results obtained 14 days after surgery demonstrate a leftward shift in mechanical thresholds after spinal lesion (FIG. 2B). The transient hypoalgesia seen immediately after lesion surgery, followed by bilateral hyperalgesia, is consistent with findings in human patients suffering from CPS following spinal injury (Bowsher, 1995; Finnerup et al., 2003; Boivie, 2005).

Figure 2C:
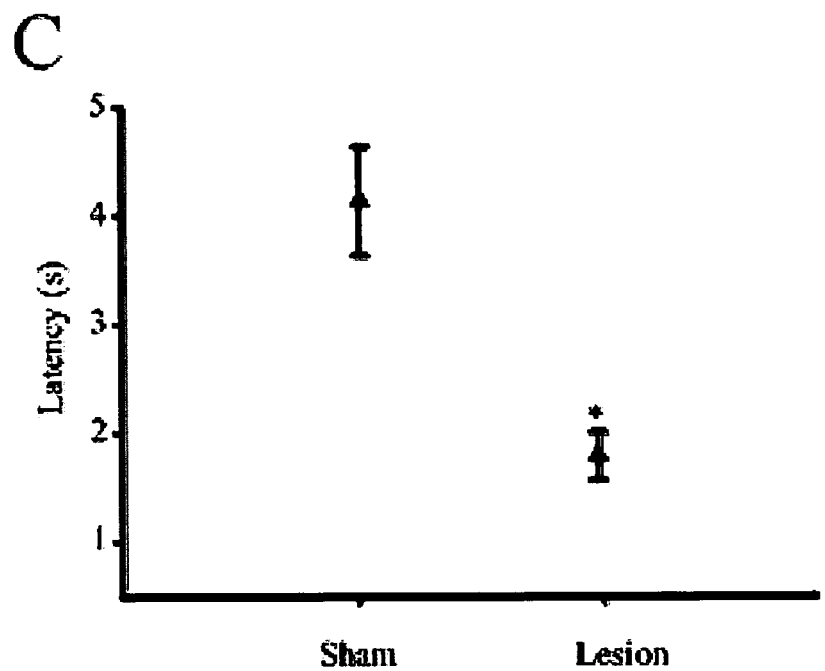

The inventors also tested responses to cold stimuli because these stimuli reliably and selectively activate nociceptors, and because cold hyperalgesia is a common complaint of CPS patients (Defrin et al., 2002b; Finnerup et al., 2003). Animals with spinal lesions (n=14) were more sensitive to cold stimuli (cold hyperalgesia) applied to the dorsal surface of the ipsilateral hindpaw, compared to sham operated control animals (n=12); Paw withdrawal latencies were 4.8±2.8 sec in sham-operate, and 1.7±1.1 sec in animals with spinal lesions (p=0.001, MWU; FIG. 2C).

Histological analyses revealed that lesions at any level between C6 and T9 produced similar CPS-like behavioral effects, consistent with findings in humans that CPS can result from lesions anywhere along the spinothalamocortical pathway (see above). As with lesions in CPS patients, our experimental lesions are unlikely to completely ablate or selectively involve the STT. Rather, as in humans, the inventors find that lesions that involve the STT result in CPS. A summary of the location and size of all lesion sites is shown in FIG. 1B. In all animals with behaviorally confirmed CPS, the lesions affected parts of the STT.

Figure 2D:
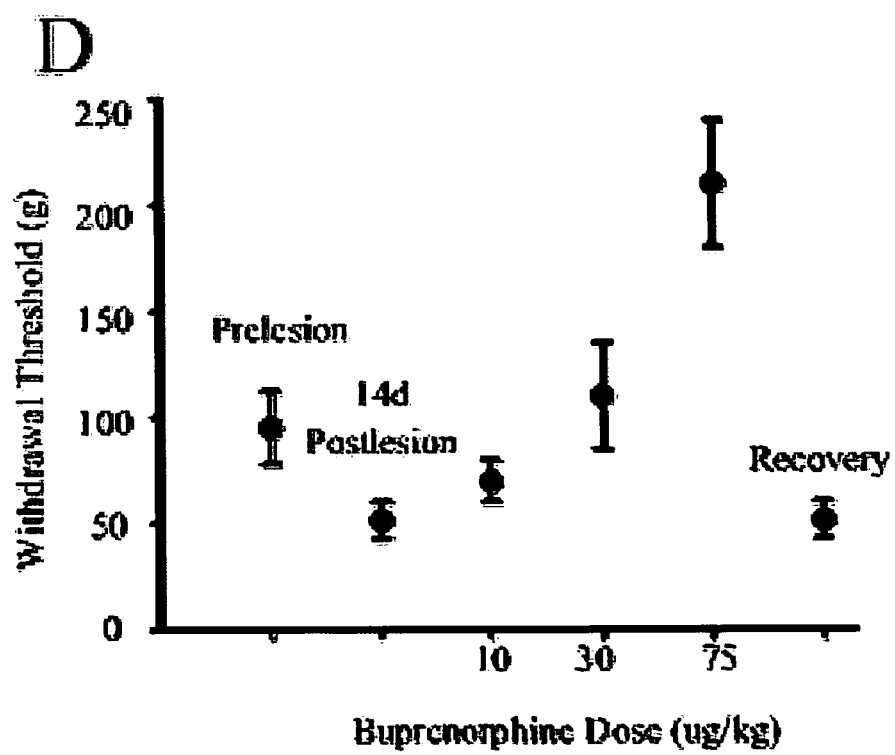

To confirm that withdrawal from mechanical stimuli reflects a response to painful stimuli, the inventors administered buprenorphine—a centrally acting opiate—to 4 animals with confirmed hyperalgesia. This resulted in a dose-dependent reversal in the reduction of hindpaw withdrawal thresholds (FIG. 2D). The effects of buprenorphine were reversible and withdrawal thresholds returned to pre-administration levels at subsequent tests. Thus, as in humans with CPS, centrally acting opiates can acutely reverse hyperalgesia, although opiates offer no long-term benefit to these patients (Eide et al., 1995; Attal et al., 2002).

Figure 2E:
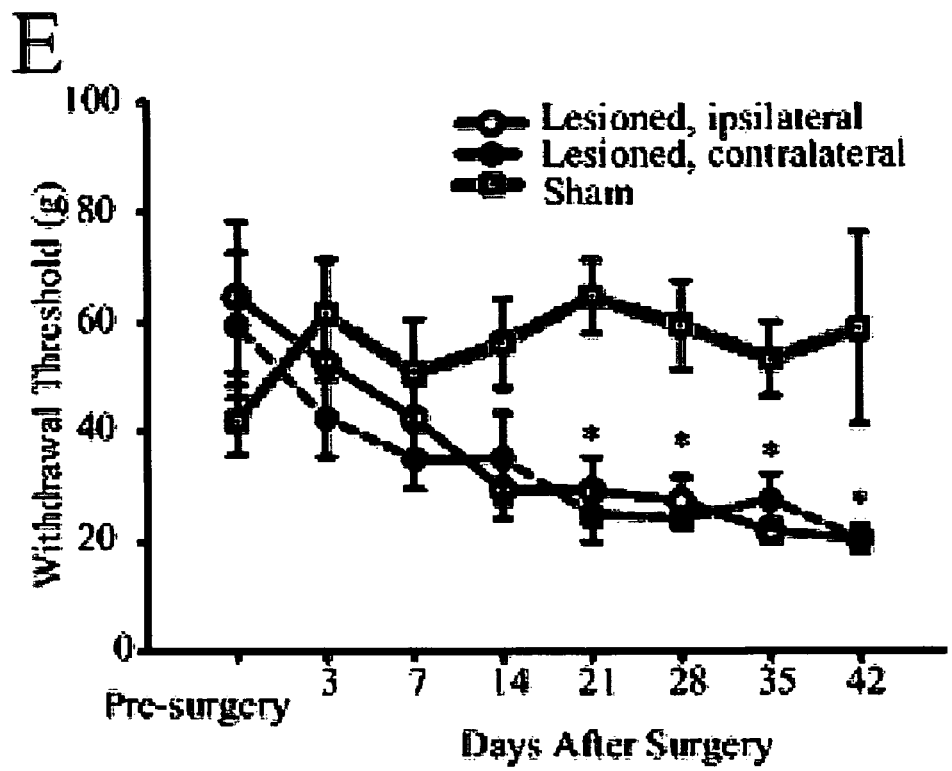
Figure 2F:
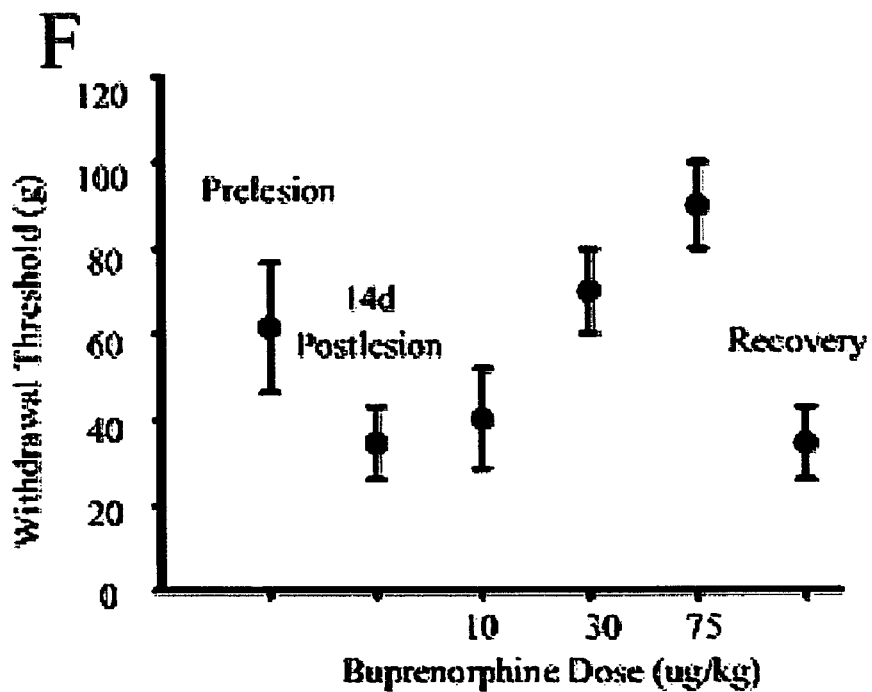

Signs of central pain were not limited to the hindpaws, as hyperalgesia extended to include the face. FIG. 2E shows that mechanical thresholds for face withdrawal began to decrease 3 days after surgery and were significantly lower than pre-lesion values at 21 days post-lesion (ipsilateral: 29±18 g, median=26 g, p=0.007, Friedman; contralateral: 25±15 g, median 26 g, p=0.007, Friedman). Similar to its effects on hindpaw hyperalgesia, buprenorphine reversed the reduction in face withdrawal thresholds in spinal-lesioned animals in a dose-dependent, reversible manner (FIG. 2F).

Consistent with previous reports in experimental animals with CPS (Stormer et al., 1997; Yezierski, 2000; Defrin et al., 2002a), these findings demonstrate that animals with spinal lesions present with diffuse, bilateral mechanical hyperalgesia that involves dermatomes below and above the lesion site. Furthermore, spinal-lesioned animals are significantly hyperalgesic to cold stimuli ipsilateral to the lesion site. Therefore, this model of central pain recapitulates clinical characteristics of CPS, as described above, and allowed for directly elucidating and testing mechanisms responsible for CPS.

Example 2

Suppressed Neuronal Activity in the ZI

The zona incerta (ZI) is aptly named: the function of this "zone of uncertainty", situated ventral to the thalamus, has been debated since Auguste Forel first described it in 1877 (Forel, 1877). ZI receives dense nociceptive inputs through the STT (Shammah-Lagnado et al., 1985; Craig, 2004), and has been implicated in a variety of functions (Yen et al., 1989; Pono et al., 2003). A striking feature of the ZI is its target specificity (Bartho et al, 2002; Mitrofanis, 2005). In all sensory systems it provides inhibitory inputs exclusively to "higher order" thalamic nuclei (e.g., posterior nucleus in the somatosensory system and the inferior pulvinar in the visual system). ZI afferents avoid first-order thalamic nuclei (e.g., ventroposterior in the somatosensory system and the lateral geniculate in the visual system).

ZI sends a dense GABAergic projection upon the posterior nucleus of the thalamus (PO) (Power et al., 1999; Bartho et al., 2002), a nucleus critically involved in nociceptive processing (Poggio and Mountcastle, 1960; Casey, 1966; Apkarian and Shi, 1994; Zhang and Giesler, 2005). The inventors recently showed that the ZI exerts potent feed-forward and tonic inhibition of PO neurons (Trageser and Keller, 2004; Trageser et al., 2006), (also see Lavallee et al., 2005). Because of these properties of the ZI the inventors hypothesized that responses or activity in the ZI are affected in CPS. To test this, the inventors recorded spontaneous and stimulus-invoked activity from well-isolated neurons in the ventro-lateral sector of the ZI (n=17 from spinal-lesioned rats and n=18 from sham-operated controls). The inventors have recently shown that essentially all cells in this sector are inhibitory neurons that project to the PO (Trageser et al., 2006). The inventors tested responses of ZI neurons to stimulation of the mystacial vibrissae—the whiskers on rats' face—because of the large somatotopic representation of the vibrissae in the ZI (Nicolelis et al., 1992), because of the reliability in which controlled stimuli can be applied, and because of the presence of lesion-induced hyperalgesia in the vibrissae pad.

Figure 3A:
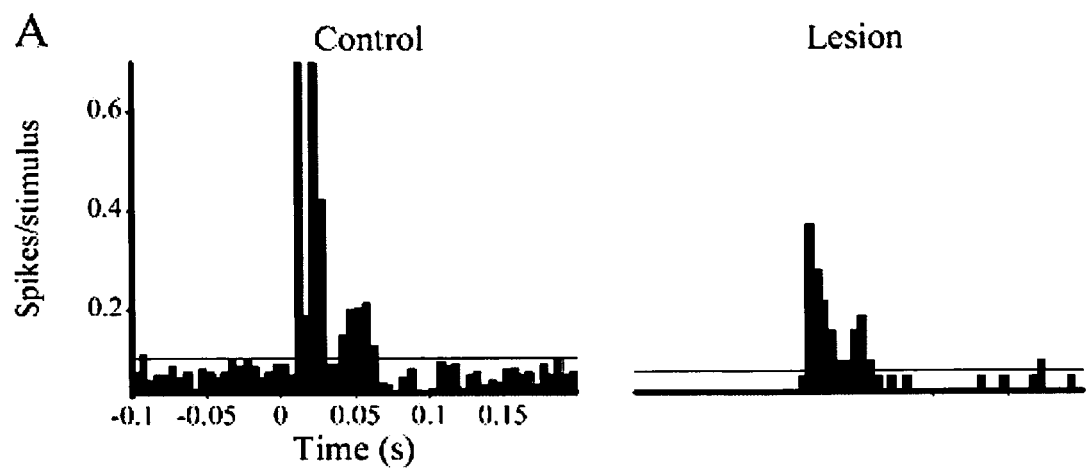
FIG. 3. Spinal lesions result in suppression of spontaneous and sensory-evoked responses of ZI neurons. (A) PSTH (1 ms bins) demonstrate that spontaneous and sensory-evoked activity in a ZI neuron recorded from a spinal-lesioned rat are markedly lower than in a control neuron. Horizontal lines represent 99% confidence interval. Group data demonstrate significant decreases in spontaneous (B) and stimulus-evoked (C) activity of ZI neurons from rats with CPS. (D) ZI stimulation reduces mechanical hyperalgesia in animals with CPS. Error bars represent SD. * indicate statistically significant difference, p<0.05, Mann Whitney U test.
Figure 3B:
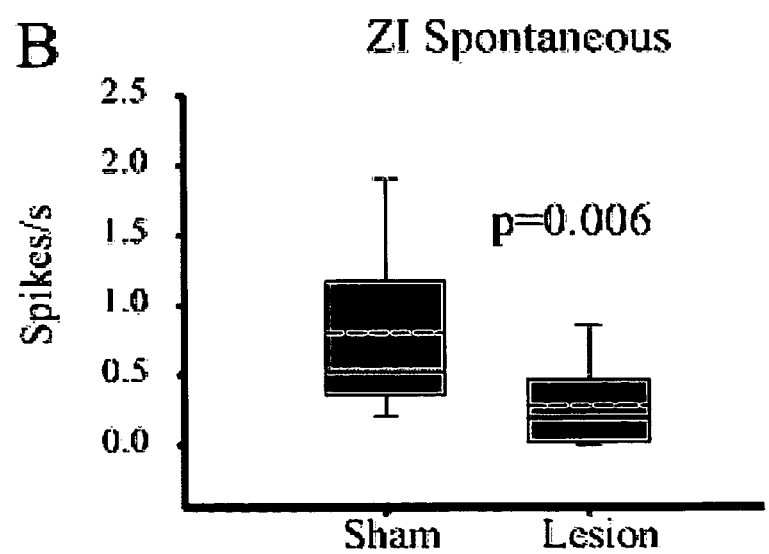
Figure 3C:
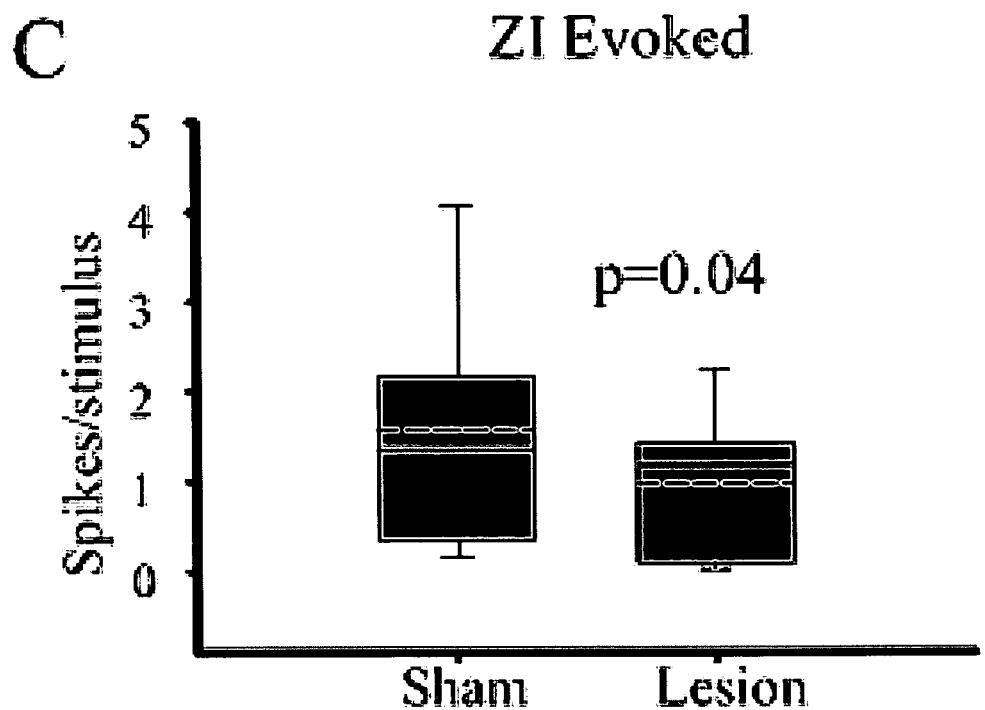

FIG. 3A compares activity recorded from a ZI neuron in a sham-operated rat (control) with activity recorded from a rat with a spinal lesion and behaviorally confirmed hyperalgesia. In the neuron recorded from the spinal-lesioned rat the spontaneous firing rate (1.6 Hz) is noticeably lower than in the neuron from the sham-operated rat (12 Hz). The magnitude of the vibrissae-evoked response in the spinal-lesioned rat (0.04 spikes/stimulus) is also markedly lower than in the sham-operated control (1.5 spikes/stimulus). As a group, ZI neurons from spinal-lesioned rats have significantly lower spontaneous firing rates (0.29±0.28 Hz vs. 0.80±0.70 Hz in shams, p=0.006, FIG. 3B), and lower vibrissae-evoked responses (1.0±0.7 spikes/stimulus vs. 1.4±1.3 spikes/stimulus in shams, p=0.04, FIG. 3C).

Example 3

ZI Stimulation Reduces Hyperalgesia

Figure 3D:
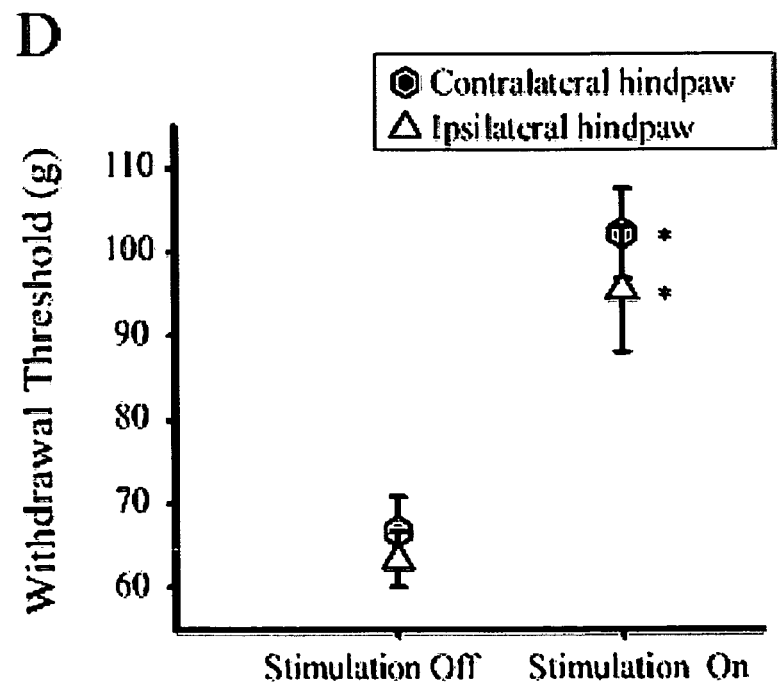

To determine if suppressed activity in the ZI is causally responsible for mechanical hyperalgesia in animals with CPS, the inventors stimulated the ZI using chronically implanted stimulation electrodes. FIG. 3D details the effect of electrical stimulation on mechanical withdrawal thresholds (n=6 rats). When the inventors applied mechanical stimuli while stimulating the ZI, withdrawal thresholds were significantly increased, and typically returned to pre-lesion levels. ZI stimulation reversed mechanical hyperalgesia in one or both of the hindpaws (range: 0-80% increase in threshold of hindpaw ipsilateral to the lesion, 25-93% increase contralaterally; p<0.05, MWU; FIG. 3D).

Example 4

Abnormally High Neuronal Activity in the PO

Because the ZI normally exerts potent tonic and feed-forward inhibition upon the PO (see above), the inventors postulated that suppressed ZI activity would result in abnormally high activity in the PO. To test this, the inventors recorded spontaneous and stimulus-evoked responses from PO neurons of spina-lesioned rats with confirmed CPS, and from sham-operated controls.

Figure 4A:
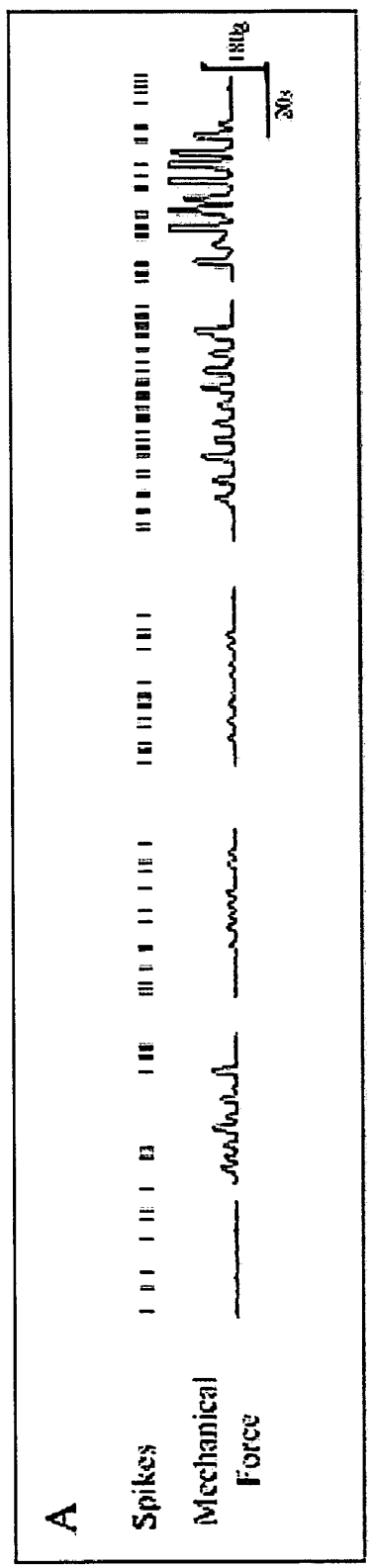
FIG. 4. Neuronal activity in the PO is enhanced in animals with central pain. (A) Representative example of responses recorded from a PO neuron in an animal with CPS. Time stamps of action potentials (upper trace) recorded during spontaneous activity, and during application (randomized order) of various mechanical forces (lower trace) to the dorsal surface of the hindpaw, using an electronic anesthesiometer. (B) In a PO neuron from a sham-operated control, spontaneous firing rate is low, and responses significantly exceed this spontaneous activity level only when strong stimuli (>180 g) are applied. This threshold is identical to the behavioral withdrawal threshold in this animal. In a neuron from the spinal-lesioned animal with confirmed CPS, spontaneous activity is higher, and both electrophysiological and behavioral threshold are considerably lower (60 g). (C) Group data showing that the activity of PO neurons is significantly higher in animals with CPS in response to mechanical hindpaw stimulation. (D) The activity of PO neurons in animals with CPS is also higher in response to vibrissae stimulation. PSTHs computed for PO neurons recorded from a sham-operated and a spinal-lesioned animal. Note the large increase in spontaneous and evoked activity. Horizontal lines represent 99% confidence interval. Spontaneous activity (E) and vibrissae-evoked activity (F) are enhanced in PO neurons recorded from spinal-lesioned animals. * statistically, significant difference, p<0.05.
Figure 4B:
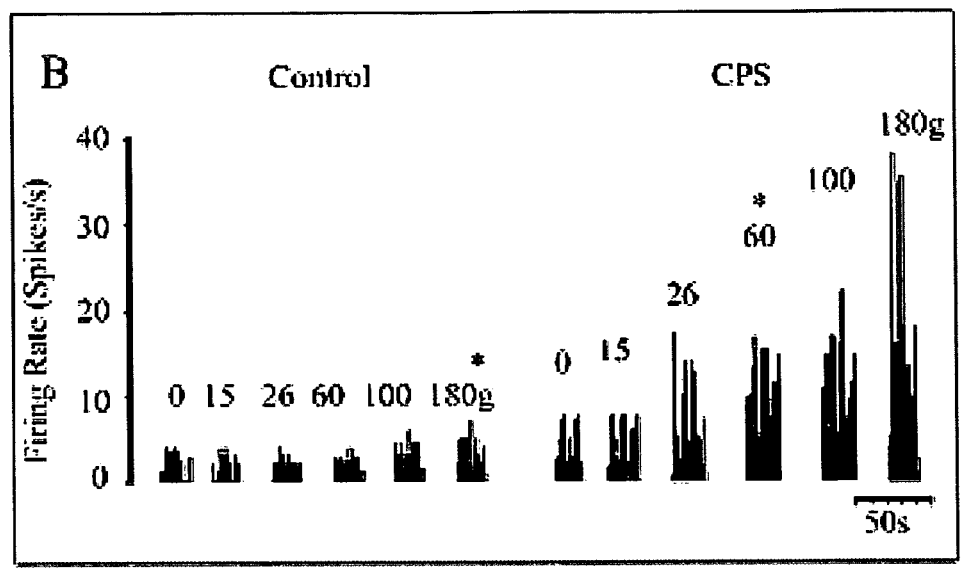

Recording from a representative PO neuron from an animal with CPS are shown in FIG. 4A. The inventors applied mechanical stimuli to the dorsal surface of the hindpaw, ipsilateral to the lesion site, with the use of an electronic anesthesiometer; force traces are shown at the bottom. Note that this neuron responds with a larger number of spikes to increasing mechanical forces. The relationship between stimulus intensity and firing rate is shown in FIG. 4B for PO neurons from a sham-operated rat ("Control") and from a spinal-lesioned rat with confirmed CPS ("CPS"). The control PO neuron fired spontaneously at low rates that were not significantly modulated by mechanical stimuli until the force applied exceeded 180 g ($p=0.019$, ANOVA); this force was identical to the one required to evoke a withdrawal response from the same animal during behavioral test sessions. In contrast, the PO neuron recorded from the rat with CPS exhibited significantly higher spontaneous activity, and responded to increasing mechanical forces with increasing firing rates. The threshold for significant responses (60 g, $p<0.0001$) corresponded to the behavioral withdrawal threshold, and both behavioral and electrophysiological thresholds were markedly lower than in the control animal.

Figure 4C:
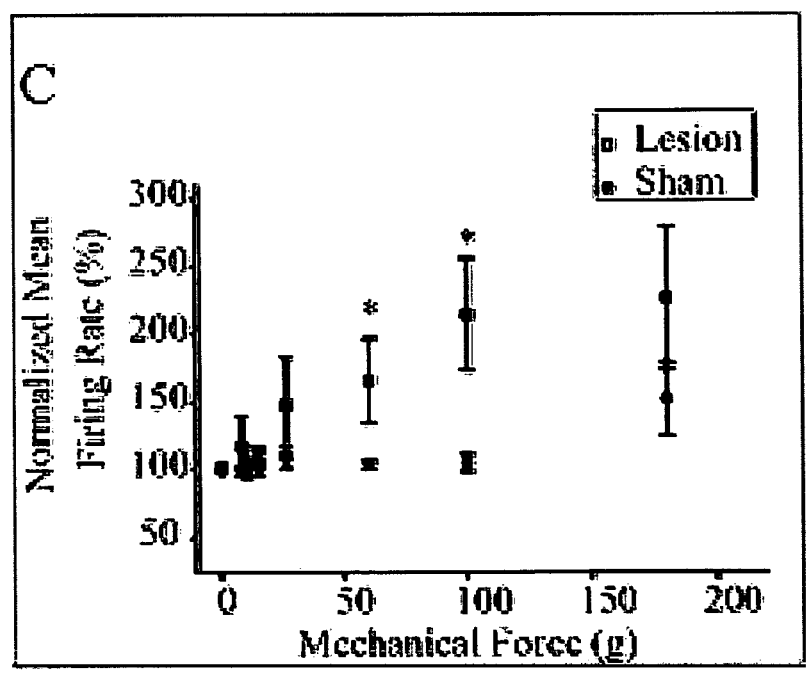
Figure 4D:
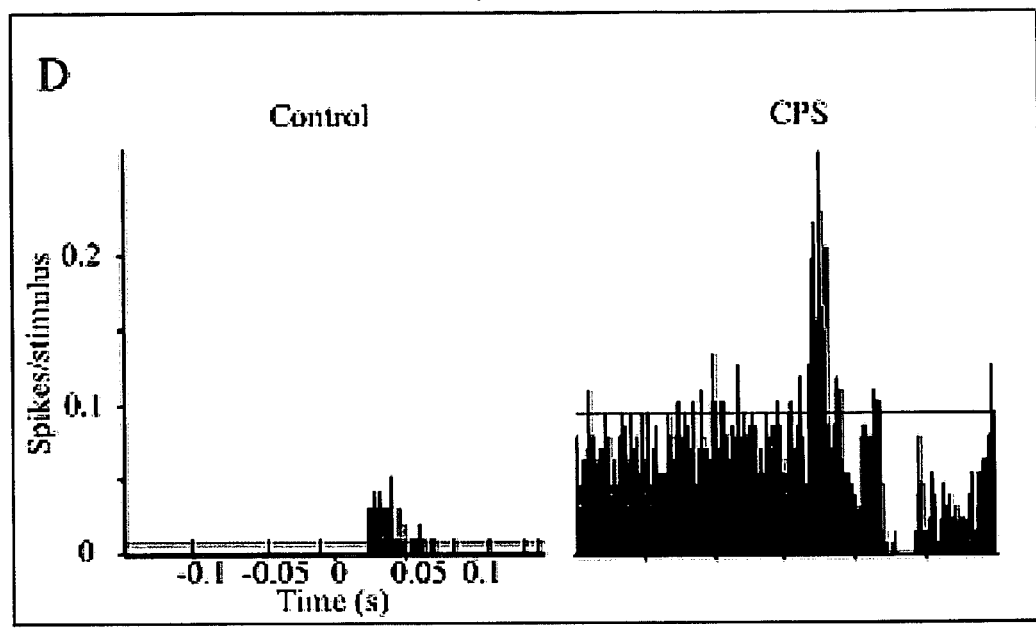
Figure 4E:
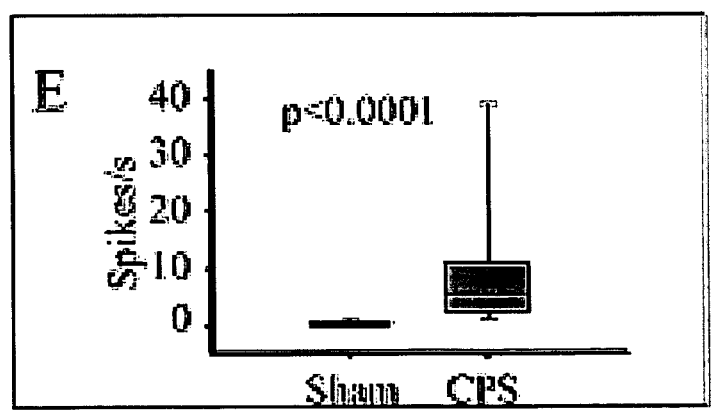

Stimulus-response curves constructed from neuronal responses to mechanical stimuli show a significant leftward shift for spinal-lesioned animals compared to shams, consistent with the leftward shift observed for the behavioral responses (sham threshold=180 g; CPS threshold=60 g, FIG. 4C). As a group, spontaneous activity in PO neurons of animals with CPS was approximately 30-fold higher than in sham-operated animals (sham: mean=0.37±0.40, median=0.2 Hz, n=12; CPS: mean=10.7±16.6 Hz, median=5.6 Hz, n=15; $p<0.0001$, MWU, FIG. 4E). In all cases, the force required to elicit a significant change from baseline (spontaneous) neuronal firing correlated with the force needed to elicit paw withdrawal in both sham-operated and spinal-lesioned animals.

Figure 4F:
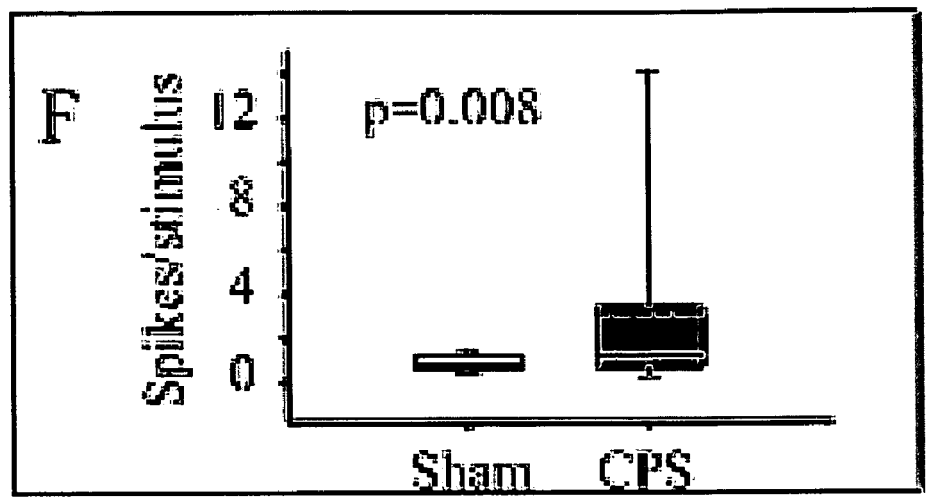

To determine if behavioral hyperalgesia in the face is also reflected in abnormal PO activity, the inventors recorded, in the same set of neurons, responses to stimulation of the vibrissae. Peristimulus histograms (PSTH) were constructed for each cell to compute response magnitude. Typical of PO neurons in control animals (Diamond et al., 1992b; Trageser and Keller, 2004; Lavallee et al., 2005), the unit depicted in FIG. 4D ("Control") exhibited low spontaneous activity and low-magnitude responses to vibrissae stimuli. In contrast, the unit recorded from an animal with CPS responded robustly to vibrissae stimuli and had a markedly high spontaneous firing rate ("CPS"). As a group, evoked response magnitudes of PO neurons from spinal-lesioned animals were significantly higher Than those of control animals (sham: mean=0.86±0.39 spikes/stimulus, median=0.60 spikes/stimulus; CPS: mean=3.2±5.6, median=1.2 spikes/stimulus, $p=0.008$, MWU, FIG. 4F).

Taken together, these results demonstrate that spinal lesions produce abnormally high spontaneous firing and enhanced PO responses to stimuli from dermatomes both below and above the lesion site. The finding that thresholds for PO responses decrease in parallel with hindpaw withdrawal thresholds demonstrate that the two phenomena are causally related, and that changes in PO responses support behavioral responses to hyperalgesia.

Example 5

Neuronal Activity in the VP Thalamus

As described herein, the ZI specifically targets "higher order" thalamic nuclei, while avoiding "first order" thalamic nuclei such as the somatosensory ventral posteromedial thalamus (VPM) and the ventral posterolateral thalamus (VPL) (Bartho et al., 2002). Because VPM and VPL activity is not regulated by ZI inputs the inventors predicted that activity in these nuclei would not be affected in animals with CPS.

Figure 5A:
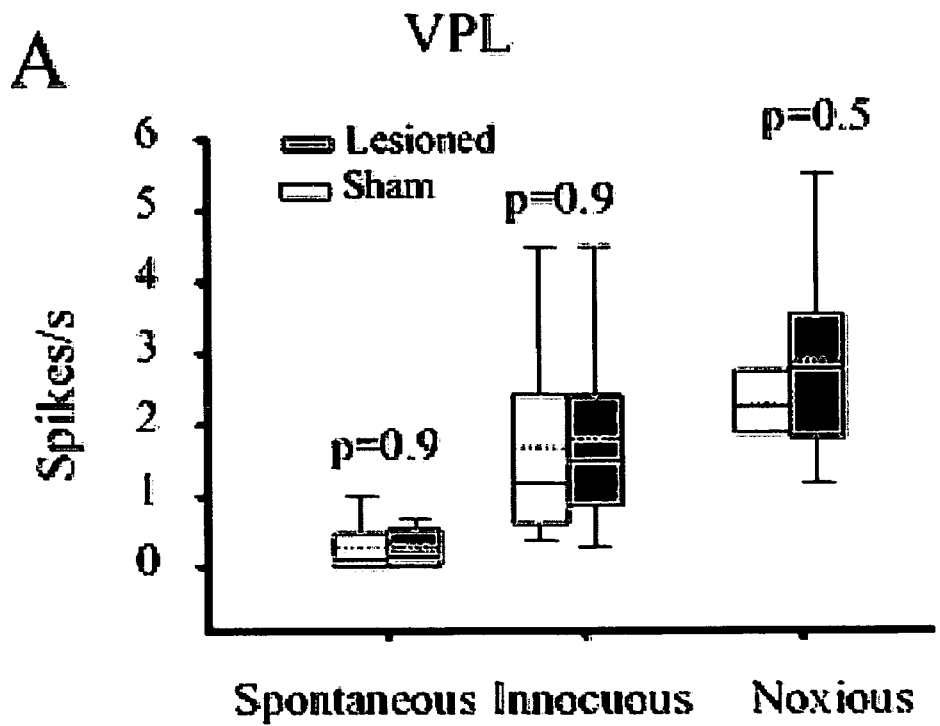
FIG. 5. (A) Spontaneous and sensory evoked responses of neurons in VPL are not significantly different between sham-operated controls and animals with CPS. (B) Sensory-evoked responses in VPM are not significantly different between control and animals with CPS. (C) In VPM, spontaneous activity was higher in animals with CPS, compared to controls. In SpVi, there were no significant differences between CPS and control animals in either spontaneous activity (D) or sensory-evoked responses (E). (F) The activity of neurons in SpVc is not significantly different between sham-operated controls and animals with CPS.

To investigate this prediction the inventors first recorded from VPL neurons that respond to hindpaw stimulation (n=12 each from spinal-lesioned rats and sham-operated controls). There was no significant difference in the magnitude of responses evoked by innocuous (50 gram) mechanical stimulation (sham: 1.70±1.39 Hz; CPS: 1.79±1.32 Hz; $p=0.9$, MWU, FIG. 5A) or noxious (120 gram) stimulation (sham: 2.28±0.43 Hz; CPS: 2.87±1.31 Hz; $p=0.5$). There was also no difference between spontaneous firing rates of neurons recorded from spinal-lesioned animals and those of sham-operated controls (sham: 0.28±0.35 Hz; CPS: 0.26±0.26 Hz; $p=0.9$ MWU, FIG. 5A). The finding that activity in VPL neurons was unaffected in CPS is consistent with the model that suppressed inhibitory inputs from the ZI to the PO is causally related to CPS.

Figure 5B:
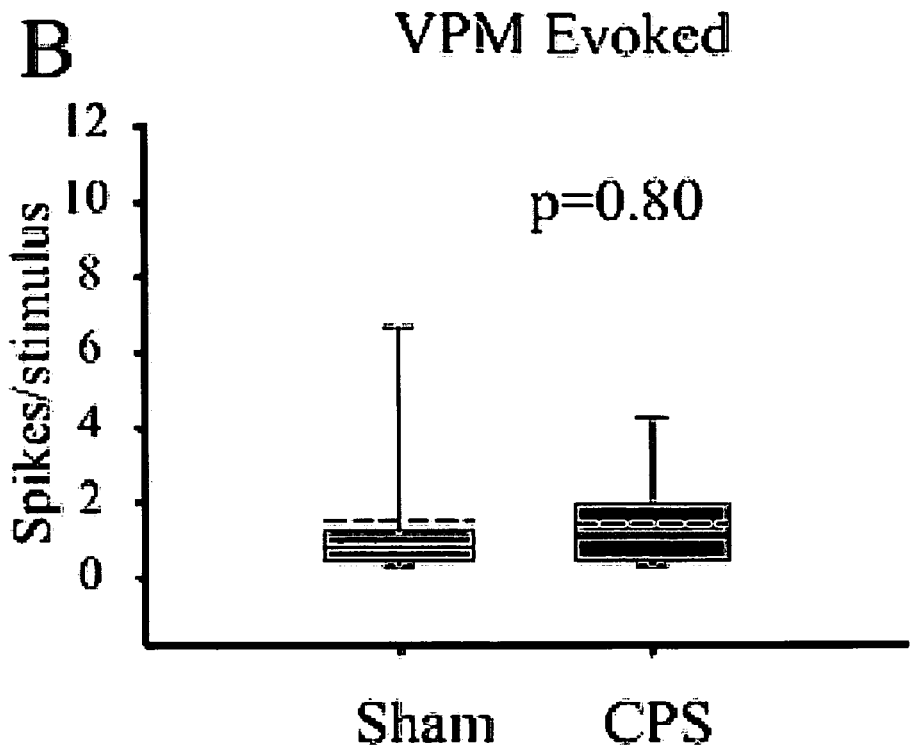
Figure 5C:
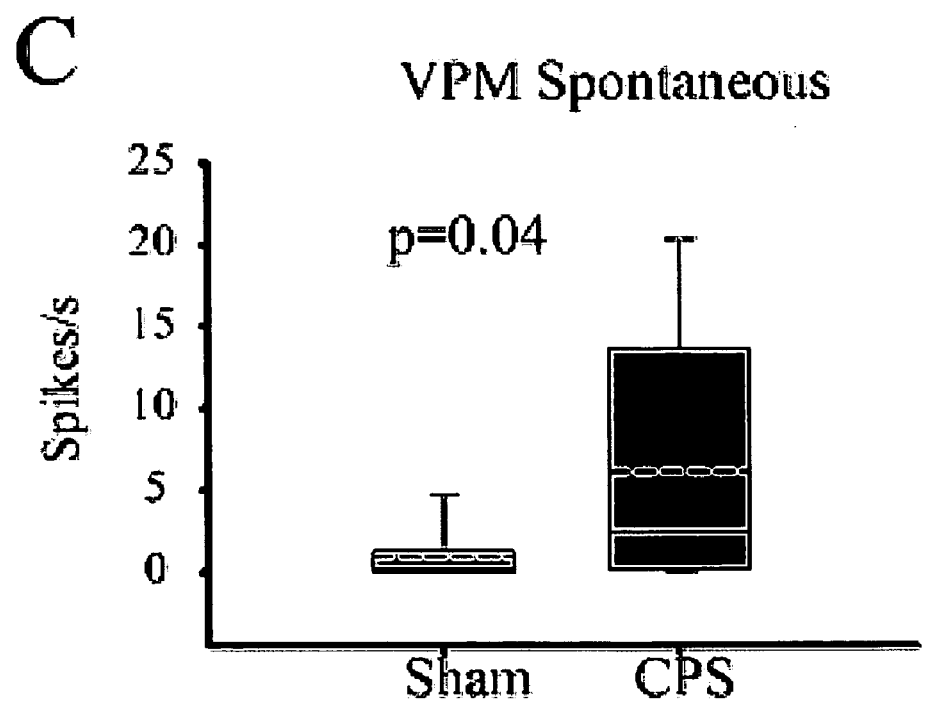

The inventors also recorded from VPM neurons that respond to innocuous vibrissae stimulation (n=10 from spinal-lesioned rats and n=13 from sham-operated controls). Consistent with our prediction, group comparisons revealed no significant difference in the magnitude of evoked responses in VPM (sham: 1.4±2.0 spikes/stimulus; CPS: 1.1±1.3 spikes/stimulus; $p=0.8$, MWU, FIG. 5B). There was, however, a modest increase in spontaneous firing rates in neurons recorded from spinal-lesioned animals (sham: 1.4±2.2 Hz; CPS: 6.2±7.5 Hz; $p=0.04$, MWU, FIG. 5C) (Compare the 30-fold increase in spontaneous activity of PO neurons with the 4-fold increase in VPM). The finding that evoked activity in VPM neurons was unaffected in CPS is consistent with the model wherein abnormalities in the ZI are responsible for the development of CPS.

Example 6

Burst Activity in Thalamus

It has been suggested previously that CPS, in both humans and animal models, is associated with abnormally high incidence of bursting activity in lemniscal thalamic nuclei (Lenz et al., 1989; Vierck et al., 1990; Weng et al., 2003; Lee et al., 2005; but see also Dostrovsky, 2007). The inventors therefore reasoned that the increased spontaneous activity in VPM might be due to an increase in the incidence of burst firing in this nucleus, as proposed previously for VPL (Wang and Thompson, 2008b). To test this prediction the inventors analyzed the incidence of bursts during spontaneous activity and in response to vibrissae stimuli. In spinal-lesioned rats there was a large and significant increase ($p=0.02$, $\chi 2$ test) in the percentage of VPM neurons that emitted bursts of 3 or more action potentials (sham: 23%; CPS: 70%). However, in bursting cells, the mean frequency of bursts was only marginally, and not significantly (p=0.06, MWU), higher in spinal-lesioned rats (sham: mean=0.02±0.05 Hz, median=0 Hz; CPS: mean=0.04±0.05 Hz, median=0.02 Hz. VPM neurons that respond with bursts to vibrissae stimulation was not significantly different between the two groups (sham: 44%, CPS: 38%; p=0.44, $\chi 2$ test). Nor was there a difference in the frequency of stimulus-evoked bursts between sham-operated and spinal-lesioned animals (sham: mean=0.01±0.03 Hz, median=0 Hz; CPS: mean=0.03±0.06 Hz, median=0.002 Hz, p=0.5, MWU).

The inventors performed similar analyses of spike bursts on PO neurons, and found no significant difference in either the percentage of spontaneously bursting cells (sham: 50%; CPS: 47%; p=0.90, $\chi 2$ test), or in the frequency of spontaneous bursts (sham: mean=0.04±0.08 Hz, median=0.002 Hz; CPS: mean=0.04±0.06 Hz, median=0 Hz, p=0.80, MWU). Similarly, neither the percentage of cells that burst in response to vibrissae stimuli (sham: 40%; CPS: 53%; p=0.30, $\chi 2$ test), nor the incidence of evoked bursts (sham: mean=0.02±0.04 Hz, median=0 Hz; CPS: mean=0.02±0.04 Hz, median=0.004 Hz, p=0.5, MWU), are significantly different in rats with CPS.

These findings indicate that the incidence of spike bursts—as defined in this study—are only marginally affected in VPM neurons, and remain unchanged in VPL and PO neurons.

Example 7

No Increase in Afferent Inputs from SpVi or SpVc

Figure 5D:
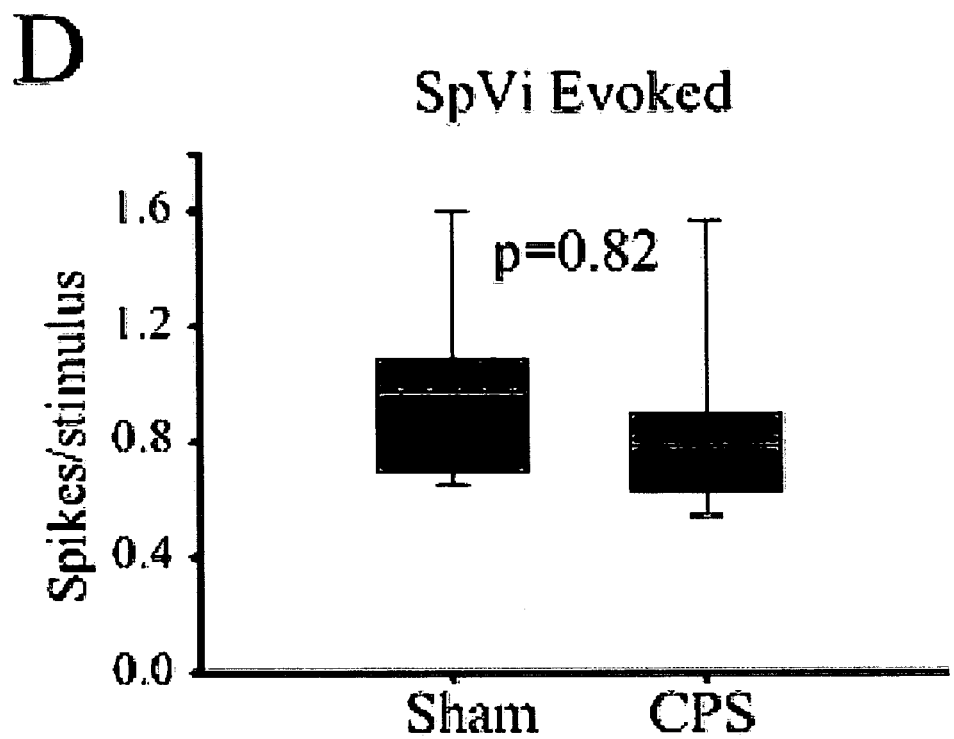
Figure 5E:
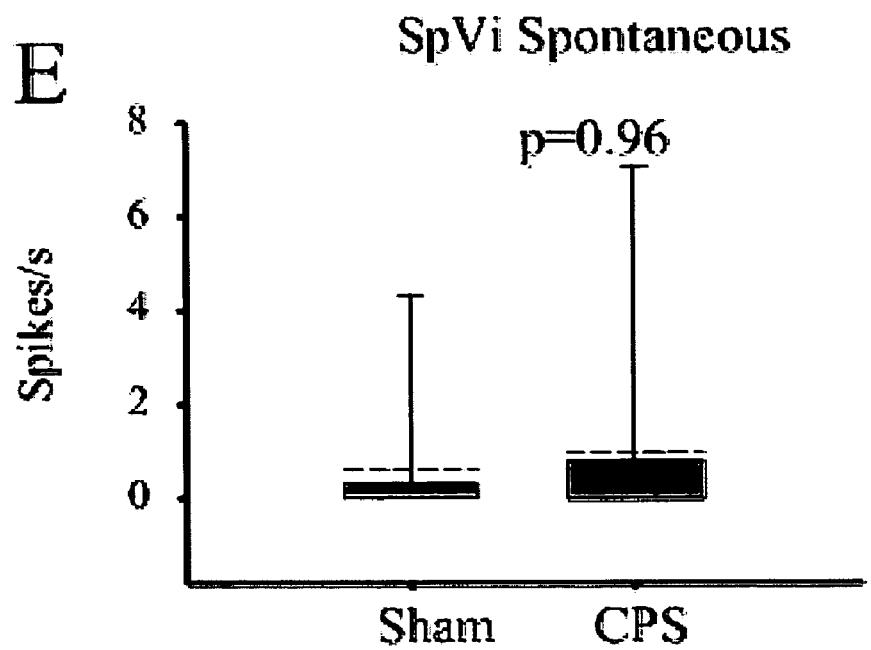

The changes in activity of PO neurons in CPS animals may reflect an increase in peripheral afferent input, rather than—or in addition to—a reduction in inhibition from the ZI. To further investigate this, the inventors recorded activity from the spinal trigeminal nucleus (SpV), the main source of afferent inputs to the PO (Veinante et al., 2000). Spontaneous firing rates of vibrissae responsive neurons in the spinal trigeminal subnucleus interpolaris (SpVi) were not significantly different between neurons recorded from sham-operated and spinal-lesioned animals (sham: mean=0.68±1.8 Hz, median=0.17 Hz, n=11; CPS: mean=0.99±2.1 Hz, median=0 Hz, n=10; p=0.96, MWU, FIG. 5D). There was also no significant difference in the magnitude of response to vibrissae stimuli (sham: mean=2.27±2.07 spikes/stimulus, median=1.47 spikes/stimulus; CPS: mean=2.03±1.18 spikes/stimulus, median=1.65 spikes/stimulus; p=0.82, MWU, FIG. 5E).

Figure 5F:
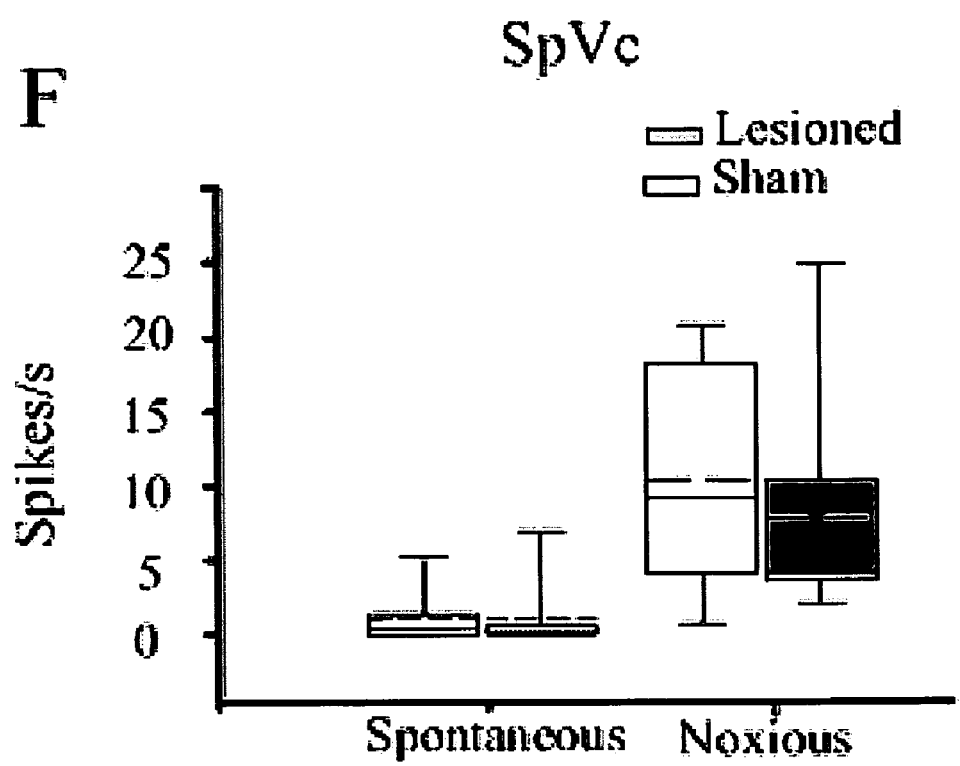

To investigate if changes in the PO reflect peripheral changes in nociceptive afferents from the face, the inventors recorded from neurons in the spinal trigeminal subnucleus caudalis (SpVc). Spontaneous firing rates of neurons in SpVc of spinal-lesioned animals were not significantly different from neurons recorded from sham-operated controls (sham: mean=1.8±2.5 Hz, n=12; CPS: mean=2.3±5.0 Hz, n=13; p=0.65, MWU, FIG. 5F). In addition, responses of these neurons to noxious mechanical stimuli applied to the face were not significantly different between the two groups (sham: mean=10.4±7.2 spikes/stimulus; CPS: mean=10.5±11.3 spikes/stimulus; p=0.53, MWU, FIG. 5F). These findings indicate that changes in PO activity in spinal-lesioned rats are not due to increased afferent inputs from SpVi or SpVc.

REFERENCES

All patents and publications mentioned in this specification are indicative of the level of those skilled in the art to which the invention pertains. All patents and publications herein are incorporated by reference to the same extent as if each individual publication was specifically and individually indicated as having been incorporated by reference in its entirety. All of the following references have been cited in this application:

Apkarian, A V, Hodge, C J (1989) Primate spinothalamic pathways: III. Thalamic terminations of the dorsolateral and ventral spinothalamic pathways. J Comp Neurol, 288: 493-511.

Apkarian, A V, Shi, T (1994) Squirrel monkey lateral thalamus. I. Somatic nociresponsive neurons and their relation to spinothalamic terminals. J Neurosci, 14:6779-6795.

Attal, N, Guirimand, F, Brasseur, L, Gaude, V, Chauvin, M, Bouhassira, D (2002) Effects of IV morphine in central pain: a randomized placebo-controlled study. Neurology, 58:554-563.

Baastrup, C, Finnerup, N B (2008) Pharmacological management of neuropathic pain following spinal cord injury. CNS Drugs, 22:455-475.

Baliki, M N, Geha, P Y, Apkarian, A V (2007) Spontaneous pain and brain activity in neuropathic pain: functional MRI and pharmacologic functional MRI studies. Curr Pain Headache Rep, 11:171-177.

Barbaresi, P, Spreafico, R, Frassoni, C, Rustioni, A (1986) GABAergic neurons are present in the dorsal column nuclei but not in the ventroposterior complex of rats. Brain Res, 382:305-326.

Bartho, P, Freund, T F, Acsady, L (2002) Selective GABAergic innervation of thalamic nuclei from zona incerta. Eur J Neurosci, 16:999-1014.

Boivie, J (2005) Central Pain. In: Wall and Melzack's Textbook of Pain (McMahon, S, Koltzenburg, M, eds), pp 1057-1074. Oxford: Churchill Livingstone.

Bokor, H, Frere, S G, Eyre, M D, Slezia, A, Ulbert, I, Luthi, A, Acsady, L (2005) Selective GABAergic control of higher-order thalamic relays. Neuron, 45:929-940. Bonica, J J (1991) History of pain concepts and pain therapy. Mt Sinai J Med, 58:191-202.

Bowsher, D (1995) Central Pain. Pain Reviews, 2:175-186.

Bowsher, D (1996) Central pain: clinical and physiological characteristics. J Neurol Neurosurg Psychiatry, 61:62-69.

Bushnell, M C, Duncan, G H (1989) Sensory and affective aspects of pain perception: is medial thalamus restricted to emotional issues? Exp Brain Res, 78:415-418.

Canavero, S, Bonicalzi, V (2007) Central Pain Syndrome: Pathophysiology, Diagnosis and Management. Cambridge Univ Press: New York.

Casey, K L (1966) Unit analysis of nociceptive mechanisms in the thalamus of the awake squirrel monkey. J Neurophysiol, 29:727-750.

Craig, A D (2004) Distribution of trigeminothalamic and spinothalamic lamina I terminations in the macaque monkey. J Comp Neurol, 477:119-148.

Craig, A D J, Burton, H (1981) Spinal and medullary lamina I projection to nucleus submedius in medial thalamus: a possible pain center. J Neurophysiol, 45:443-466.

Dammerman, R S, Flint, A C, Noctor, S, Kriegstein, A R (2000) An excitatory GABAergic plexus in developing neocortical layer 1. J Neurophysiol, 84:428-434434.

Defrin, R, Ohry, A, Blumen, N, Urca, G (2002a) Pain following spinal cord injury. Spinal Cord, 40:96-7; author reply 98-9.

Defrin, R, Ohry, A, Blumen, N, Urca, G (2002b) Sensory determinants of thermal pain. Brain, 125:501-510.

Dejerine, J, Roussy, G (1906) Le syndrome thalamique. Rev Neurol, 15:521-532.

Diamond, M E, Armstrong-James, M, Budway, M J, Ebner, F F (1992a) Somatic sensory responses in the rostral sector of the posterior group (POm) and in the ventral posterior medial nucleus (VPM) of the rat thalamus: dependence on the barrel field cortex. J Comp Neurol, 319:66-84.

Diamond, M E, Armstrong-James, M, Ebner, F F (1992b) Somatic sensory responses in the rostral sector of the posterior group (POm) and in the ventral posterior medial nucleus (VPM) of the rat thalamus. J Comp Neurol, 318: 462-476.

Dostrovsky, J O (2007) The thalamus and human pain. In: Central Neuropathic Pain: Focus on Poststroke Pain (Henry, J L, Panju, A, Yashpal, K, eds), pp 101-112. Seattle: IASP Press.

Dostrovsky, J O, Guilbaud, G (1990) Nociceptive responses in medial thalamus of the normal and arthritic rat. Pain, 40:93-104.

Edinger, L (1891) Giebt es central entstehende Schmerzen? Deutsche Zeitschrift für Nervenheilkunde, 1:262-282.

Eide, P K, Stubhaug, A, Stenehjem, A E (1995) Central dysesthesia pain after traumatic spinal cord injury is dependent on N-methyl-D-aspartate receptor activation. Neurosurgery, 37:1080-1087.

Endo, T, Spenger, C, Hao, J, Tominaga, T, Wiesenfeld-Hallin, Z, Olson, L, Xu, X J (2008) Functional MRI of the brain detects neuropathic pain in experimental spinal cord injury. Pain, Finnerup, N B, Johannesen, I L, Fuglsang-Frederiksen, A, Bach, F W, Jensen, T S (2003) Sensory function in spinal cord injury patients with and without central pain. Brain, 126:57-70.

Foix, C, Thevenard, A, Nicolesco, M (1922) Algie faciale dórigine bulbo-trigéminale au cours de la syringomyélie. Troubles sympathiques concomitants. Douleur á type cellulaire. Revue Neurologique, 29:990-999.

Forel, A (1877) Untersuchungen über die haubenregion und ihre oberen verknüpfungen im gehirne des menschen und einiger saügethiere, mit beiträgen zu den methoden der gehirnuntersuchung. Arch Psychiat Nervenkr, 7:393-495.

Giesler, G J J, Spiel, H R, Willis, W D (1981) Organization of spinothalamic tract axons within the rat spinal cord. J Comp Neurol, 195:243-252.

Greenspan, J D, Ohara, S, Sarlani, E, Lenz, F A (2004) Allodynia in patients with post-stroke central pain (CPSP) studied by statistical quantitative sensory testing within individuals. Pain, 109:357-366.

Guido, W, Lu, S M, Vaughan, J W, Godwin, D W, Sherman, S M (1995) Receiver operating characteristic (ROC) analysis of neurons in the cat's lateral geniculate nucleus during tonic and burst response mode. V is Neurosci, 12:723-741.

Head, H, Holmes, G (1911) Sensory disturbances from cerebral lesions. Brain, 34:102-254.

Jones, E G (2007) The Thalamus. Cambridge Univ. Press: Cambridge.

Kim, J H, Greenspan, J D, Coghill, R C, Ohara, S, Lenz, F A (2007) Lesions limited to the human thalamic principal somatosensory nucleus (ventral caudal) are associated with loss of cold sensations and central pain. J Neurosci, 27:4995-5004.

Lavallee, P, Urbain, N, Dufresne, C, Bokor, H, Acsady, L, Deschenes, M (2005) Feedforward inhibitory control of sensory information in higher-order thalamic nuclei. Neurosci, 25:7489-7498.

Lee, J I, Ohara, S, Dougherty, P M, Lenz, F A (2005) Pain and temperature encoding in the human thalamic somatic sensory nucleus (Ventral caudal): inhibition-related bursting evoked by somatic stimuli. J Neurophysiol, 94:1676-1687.

Lenz, F A, Kwan, H C, Dostrovsky, J O, Tasker, R R (1989) Characteristics of the bursting pattern of action potentials that occurs in the thalamus of patients with central pain. Brain Res, 496:357-360.

Ling, C Y, Schneider, G E, Northmore, D, Jhaveri, S (1997) Afferents from the colliculus, cortex, and retina have distinct terminal morphologies in the lateral posterior thalamic nucleus. J Comp Neurol, 388:467-483.

Liu, X B, Jones, E G (1999) Predominance of corticothalamic synaptic inputs to thalamic reticular nucleus neurons in the rat. J Comp Neurol, 414:67-79.

Lu, S M, Guido, W, Sherman, S M (1992) Effects of membrane voltage on receptive field properties of lateral geniculate neurons in the cat: contributions of the low-threshold $Ca^{2+}$ conductance. J Neurophysiol, 68:2185-298.

MacGowan, D J, Janal, M N, Clark, W C, Wharton, R N, Lazar, R M, Sacco, R L, Mohr, J P (1997) Central poststroke pain and Wallenberg's lateral medullary infarction: frequency, character, and determinants in 63 patients. Neurology, 49:120-125.

Masri, R, Bezdudnaya, T, Trageser, J C, Keller, A (2008) Encoding of stimulus frequency and sensor motion in the posterior medial thalamic nucleus. J Neurophysiol, 100: 681-689.

Masri, R, Trageser, J C, Bezdudnaya, T, Li, Y, Keller, A (2006) Cholinergic regulation of the posterior medial thalamic nucleus. J Neurophysiol, 96:2265-2273.

Merskey, H, Bogduk, N (1994) Classification of Chronic Pain. IASP Press: Seattle. Mills, C D, Grady, J J, Hulsebosch, C E (2001) Changes in exploratory behavior as a measure of chronic central pain following spinal cord injury. J Neurotrauma, 18:1091-1105.

Mitrofanis, J (2005) Some certainty for the "zone of uncertainty"? Exploring the function of the zona incerta. Neuroscience, 130:1-15.

Nicolelis, M A, Chapin, J K, Lin, R C (1992) Somatotopic maps within the zona incerta relay parallel GABAergic somatosensory pathways to the neocortex, superior colliculus, and brainstem. Brain Res, 577:134-141.

Nicolelis, M A, Chapin, J K, Lin, R C (1995) Development of direct GABAergic projections from the zona incerta to the somatosensory cortex of the rat. Neuroscience, 65:609-631.

Peyron, R, Laurent, B, Garcia-Larrea, L (2000) Functional imaging of brain responses to pain. A review and meta-analysis (2000). Neurophysiol Clin, 30:263-288.

Pierret, T, Lavallee, P, Deschenes, M (2000) Parallel streams for the relay of vibrissal information through thalamic barreloids. J Neurosci, 20:7455-7462.

Poggio, G F, Mountcastle, V B (1960) A study of the functional contributions of the lemniscal and spinothalamic systems to somatic sensibility. Central nervous mechanisms in pain. Bull Johns Hopkins Hosp, 106:266-316.

Porro, C A, Cavazzuti, M, Lui, F, Giuliani, D, Pellegrini, M, Baraldi, P (2003) Independent time courses of supraspinal nociceptive activity and spinally mediated behavior during tonic pain. Pain, 104:291-301.

Power, B D, Kolmac, C I, Mitrofanis, J (1999) Evidence for a large projection from the zona incerta to the dorsal thalamus. J Comp Neurol, 404:554-565.

Power, B D, Mitrofanis, J (2002) Ultrastructure of afferents from the zona incerta to the posterior and parafascicular thalamic nuclei of rats. J Comp Neurol, 451:33-44. Physiol Behav, 67:711-716.

Ren, K (1999) An improved method for assessing mechanical allodynia in the rat. Physiol Behav, 67:711-716.

Sceniak, M P, Maciver, M B (2006) Cellular actions of urethane on rat visual cortical neurons in vitro. J Neurophysiol, 95:3865-3874.

Schmahmann, J D, Leifer, D (1992) Parietal pseudothalamic pain syndrome. Clinical features and anatomic correlates. Arch Neurol, 49:1032-1037.

Shammah-Lagnado, S J, Negrao, N, Ricardo, J A (1985) Afferent connections of the zona incerta: a horseradish peroxidase study in the rat. Neuroscience, 15:109-134.

Shaw, V E, Mitrofanis, J (2001) Lamination of spinal cells projecting to the zona incerta of rats. J Neurocytol, 30:695-704.

Sherman, S M (1996) Dual response modes in lateral geniculate neurons: mechanisms and functions. V is Neurosci, 13:205-213.

Siddall, P, Xu, C L, Cousins, M (1995) Allodynia following traumatic spinal cord injury in the rat. Neuroreport, 6:1241-1244.

Stormer, S, Gerner, H J, Gruninger, W, Metzmacher, K, Follinger, S, Wienke, C, Aldinger, W, Walker, N, Zimmermann, M, Paeslack, V (1997) Chronic pain/dysaesthesiae in spinal cord injury patients: results of a multicentre study. Spinal Cord, 35:446-455.

Tasker, R R (1991) Meralgia paresthetica. J Neurosurg, 75:168.

Tasker, R R, Organ, L W, Hawrylyshyn, P A (1982) The thalamus and midbrain of man: a physiological atlas using electrical stimulation. C. C. Thomas: Springfield, Ill.

Trageser, J C, Burke, K A, Masri, R, Li, Y, Sellers, L, Keller, A (2006) State-dependent gating of sensory inputs by zona incerta. J Neurophysiol, 96:1456-1463.

Trageser, J C, Keller, A (2004) Reducing the uncertainty: gating of peripheral inputs by zona incerta. J Neurosci, 24:8911-8915.

Varela, C, Sherman, S M (2007) Differences in response to muscarinic activation between first and higher order thalamic relays. J Neurophysiol, 98:3538-3547.

Veinante, P, Jacquin, M F, Deschenes, M (2000) Thalamic projections from the whisker-sensitive regions of the spinal trigeminal complex in the rat. J Comp Neurol, 420:233-243.

Vierck, C J J, Greenspan, J D, Ritz, L A (1990) Long-term changes in purposive and reflexive responses to nociceptive stimulation following anterolateral chordotomy. J Neurosci, 10:2077-2095.

Villarreal, C F, Kina, V A, Prado, W A (2004) Antinociception induced by stimulating the anterior pretectal nucleus in two models of pain in rats. Clin Exp Pharmacol Physiol, 31:608-613.

Villarreal, C F, Prado, W A (2007) Modulation of persistent nociceptive inputs in the anterior pretectal nucleus of the rat. Pain, 132:42-52.

Wang, G, Thompson, S M (2008a) Maladaptive homeostatic plasticity in a rodent model of central pain syndrome: thalamic hyperexcitability after spinothalamic tract lesions. J Neurosci, 28:11959-11969.

Wang, G, Thompson, S M (2008b) Maladaptive homeostatic plasticity in a rodent model of central pain syndrome: thalamic hyperexcitability after spinothalamic tract lesions. J Neurosci, in press Weng, H R, Lenz, F A, Vierck, C, Dougherty, P M (2003) Physiological changes in primate somatosensory thalamus induced by deafferentation are dependent on the spinal funiculi that are sectioned and time following injury. Neuroscience, 116:1149-1160.

Yen, C T, Fu, T C, Chen, R C (1989) Distribution of thalamic nociceptive neurons activated from the tail of the rat. Brain Res, 498:118-122.

Yezierski, R P (2000) Pain following spinal cord injury: pathophysiology and central mechanisms. Prog Brain Res, 129:429-449.

Zhang, X, Giesler, G J J (2005) Response characteristics of spinothalamic tract neurons that project to the posterior thalamus in rats. J Neurophysiol, 93:2552-2564.

What is claimed is:

1. A method of treating a symptom of central pain syndrome (CPS) in an individual in need thereof comprising electrically stimulating the zona incerta (ZI) region of the brain of an individual having CPS in an amount sufficient to increase GABAergic neuron firing, wherein the stimulating occurs at a frequency of between about 0.1 Hz to 900 Hz.

2. The method of claim 1, wherein the electrical stimulation is transcranial electrical stimulation.

3. The method of claim 1, wherein the electrical stimulation is subcranial electrical stimulation.

4. The method of claim 3, wherein the subcranial electrical stimulation is achieved by an electrode implanted adjacent to or directly in the ZI.

5. The method of claim 4, wherein the subcranial electrical stimulation is applied at a frequency of 1 Hz to 100 Hz.

6. The method of claim 4, wherein the al electrical stimulation is applied at an intensity of 5 µA to 1 mA.

7. The method of claim 4, wherein the subcranial electrical stimulation is applied at a frequency of 50 Hz and an intensity of 25 µA.

8. A method of treating a hyperalgesia in an individual in need thereof comprising electrically stimulating the zona incerta (ZI) region of the brain of an individual having hyperalgesia in an amount sufficient to increase GABAergic neuron firing, wherein the stimulating occurs at a frequency of between about 0.1 Hz to 900 Hz.

9. The method of claim 8, wherein the electrical stimulation is transcranial electrical stimulation.

10. The method of claim 8, wherein the electrical stimulation is subcranial electrical stimulation.

11. The method of claim 10, wherein the subcranial electrical stimulation that is achieved by an electrode implanted adjacent to or directly in the ZI.

12. The method of claim 11, wherein the subcranial electrical stimulation is applied at a frequency of 1 Hz to 100 Hz.

13. The method of claim 11, wherein the subcranial electrical stimulation is applied at an intensity of 5 µA to 1 mA.

14. The method of claim 11, wherein the subcranial electrical stimulation is applied at a frequency of 50 Hz and an intensity of 25 µA.

* * * * *